US012705397B2

(12) United States Patent
Chiu et al.

(10) Patent No.: US 12,705,397 B2
(45) **Date of Patent: *Aug. 11, 2026**

(54) RESOURCE-EFFICIENT PRIVACY-PRESERVING TRANSACTIONS

(71) Applicant: Enya Inc., Palo Alto, CA (US)

(72) Inventors: Alan N. Chiu, Palo Alto, CA (US); Jan T. Liphardt, Palo Alto, CA (US)

(73) Assignee: Enya Inc., Palo Alto, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 18/740,498

(22) Filed: Jun. 11, 2024

(65) Prior Publication Data

US 2024/0330517 A1 Oct. 3, 2024

Related U.S. Application Data

(63) Continuation of application No. 17/135,917, filed on Dec. 28, 2020, now Pat. No. 12,067,151, which is a
(Continued)

(51) Int. Cl.
*G06F 21/62* (2013.01)
*G16H 10/60* (2018.01)

(52) U.S. Cl.
CPC ...... *G06F 21/6263* (2013.01); *G06F 21/6254* (2013.01); *G16H 10/60* (2018.01)

(58) Field of Classification Search
CPC . G06F 21/6245; G06F 21/60; G06Q 2220/10; G06Q 2220/16; H04L 2209/60; H04L 2209/605
See application file for complete search history.

(56) References Cited

U.S. PATENT DOCUMENTS

| | | | |
|---|---|---|---|
| 5,852,811 | A | 12/1998 | Atkins |
| 6,456,979 | B1 | 9/2002 | Flagg |

(Continued)

FOREIGN PATENT DOCUMENTS

| | | | | |
|---|---|---|---|---|
| DE | 102015208142 A1 | 11/2015 | | |
| EP | 2485430 A2 * | 8/2012 | ............... | H04L 9/40 |
| WO | WO-2019086429 A1 * | 5/2019 | ......... | G06F 21/6227 |

OTHER PUBLICATIONS

"All the Sensors in Your Smartphone, and How They Work", Neld, David, dated Jul. 23, 2017, 6 pages.

(Continued)

*Primary Examiner* — Esther B. Henderson
(74) *Attorney, Agent, or Firm* — Patrick E. Caldwell, Esq.; The Caldwell Firm, PLLC

(57) ABSTRACT

A computer with data (the "source") establishes communication channels to other computers with available computing resources (the "workers"). The computers exchange information to negotiate alternative sets of encryption techniques and security settings. The source calculates a response by negotiating a data reduction scheme that is applied to form heterogeneous data payloads. Some of the data are encrypted using a fully homomorphic encryption algorithm to form a multi-segment response, whereas other data are encrypted using an encryption algorithm other than fully homomorphic encryption. Security-relevant parameters of the invoked encryption schemes are varied to achieve a negotiated optimal data reduction scheme. Candidate reduction schemes to apply to the user data are negotiated based on then-current communication bandwidth availability and/or computer processing resources at the source and/or at the workers. When an agreement is reached, the source transmits protected data to the workers in accordance with the negotiated data reduction scheme.

20 Claims, 20 Drawing Sheets

Related U.S. Application Data continuation-in-part of application No. 16/894,875, filed on Jun. 7, 2020, now abandoned, and a continuation-in-part of application No. 16/824,223, filed on Mar. 19, 2020, now Pat. No. 11,461,499, and a continuation-in-part of application No. 16/537,523, filed on Aug. 9, 2019, now Pat. No. 10,878,950, said application No. 16/824,223 is a continuation of application No. 16/400,030, filed on Apr. 30, 2019, now Pat. No. 10,635,837.

(56) References Cited

U.S. PATENT DOCUMENTS

| | | | | |
|---|---|---|---|---|
| 7,197,642 | B2 | 3/2007 | Walmsley | |
| 7,392,201 | B1 | 6/2008 | Binns et al. | |
| 7,685,007 | B1 | 3/2010 | Jacobson | |
| 2002/0052761 | A1 | 5/2002 | Fey et al. | |
| 2003/0009355 | A1 | 1/2003 | Gupta | |
| 2003/0036081 | A1 | 2/2003 | Adorjan et al. | |
| 2005/0091101 | A1 | 4/2005 | Epling et al. | |
| 2005/0208941 | A1 | 9/2005 | Ordille et al. | |
| 2005/0234742 | A1 | 10/2005 | Hodgdon | |
| 2005/0255458 | A1 | 11/2005 | Polansky | |
| 2005/0282213 | A1 | 12/2005 | Halle | |
| 2006/0147947 | A1 | 7/2006 | Apfeld et al. | |
| 2008/0228765 | A1 | 9/2008 | Kenedy et al. | |
| 2009/0094065 | A1 | 4/2009 | Hyde et al. | |
| 2010/0311813 | A1 | 12/2010 | Kerner et al. | |
| 2011/0235697 | A1 | 9/2011 | Fallon | 375/240 |
| 2014/0281511 | A1 | 9/2014 | Kaushik | 713/189 |
| 2014/0289536 | A1 | 9/2014 | MacCarthy | 713/164 |
| 2014/0359287 | A1 | 12/2014 | Veugen | 713/167 |
| 2015/0227697 | A1 | 8/2015 | Nelson et al. | |
| 2015/0304331 | A1 | 10/2015 | Nakagawa | 726/28 |
| 2016/0328621 | A1 | 11/2016 | Negi et al. | |
| 2017/0005787 | A1 | 1/2017 | Weaver | |
| 2018/0101697 | A1 | 4/2018 | Rane et al. | |
| 2018/0234234 | A1 | 8/2018 | Hurley et al. | |
| 2019/0124051 | A1 | 4/2019 | Soon-Shiong | |
| 2019/0156426 | A1 | 5/2019 | Drucker et al. | |
| 2019/0199509 | A1 | 6/2019 | Hoshizuki | |
| 2019/0229907 | A1 | 7/2019 | Nicolson et al. | |
| 2020/0195618 | A1 | 6/2020 | Linton | |
| 2020/0311299 | A1 | 10/2020 | Amar | |

OTHER PUBLICATIONS

"FeatureMatch: A General ANNF Estimation Technique and its Applications", Ramakanth, A., dated Mar. 3, 2014, 2 pages.
"Metal: Blazing Fast Image Processing", Parziale, G., Jan. 5, 2016, 10 pages.
"Photo Editing with Generative Adversarial Networks (Part 1) NVIDIA Developer Blog", Heinrich, G., Apr. 20, 2017, 13 pages.
"PointNet—Deep Hierarchical Feature Learning on Point Sets in a Metric Space", QI, Charles et al., 2017, 2 pages.
"Efficient Variants of the ICP Algorithm", Rusenkeiwicz, S., May 28, 2001, 8 pages.
"PointNetPlusPlus", QI, Charles et al., 2017, 10 pages.
"Siamese Neural Networks for One-shot Image Recognition", Koch, Gregory, 2015, 8 pages.
"SSD: Single Shot MultiBox Detector", Liu, Wei, Dec. 29, 2016, 17 pages.
"Privacy in Pharmacogenetics", Fredrikson, Matthew, "23rd USENIX Security Symposium", dated Aug. 22, 2014, 17 pages.
"Similarity Search in High Dimensions via Hashing", Gionis, Aristides, "Proceedings of the 25th VLDB Conference", dated Sep. 7, 1999, 12 pages.
"Patient Privacy in the Era of Big Data", Kayaalp, Mehmet, "Balkan Med J 2018", dated Sep. 11, 2017, 10 pages.
"The Algorithmic Foundations of Differential Privacy", Dwork, Cynthia, "Foundations of Trends in Theoretical Computer Science", dated Jan. 1, 2014, 281 pages.
"What is Differential Privacy", Green, Matthew, "https://blog.cryptographyengineering.com/2016/06/15/what-is-differential-privacy/", dated Jun. 15, 2016, 8 pages.
"Actively Secure Two-party Computation", Pullonen, Pille, dated May 20, 2013, 101 pages.
"Efficient Multiparty Protocols Using Circuit Randomization", Beaver, Donald, dated Aug. 11, 1991, 13 pages.
"Invasion of Privacy: Tracking Your Online Behavior Across the Web", Lindsey, Nicole, dated Dec. 6, 2017, 8 pages.
"Round and Communication Efficient Unconditionally-Secure Mpc With T<N/3 In Partially Synchronous Network", Choudhury, A et al. dated 2017, 27 pages.
"Catching MPC Cheaters" Cunningham, R., et al., dated 2017, 25 pages.
"Deanonymization and linkability of cryptocurrency transactions based on network analysis" Biryukov et al., "IEEE European symposium on security and privacy (EuroS&P)", dated 2019, 13 pages.

* cited by examiner

6B00

6C00

6D00

6B00
Optimization Priority (Type #1 Computations)
Payload Size
10
8
6
4
2
0
Security
Deniability
Computation Latency
Expression Complexity
Compute Platform Resources

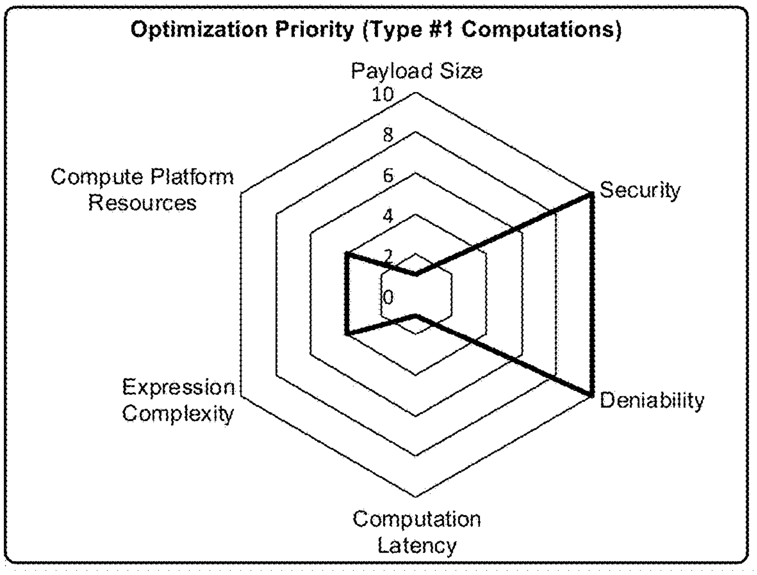

FIG. 6B
6C00
Optimization Priority (Type #2 Computations)
Payload Size
10
8
6
4
2
0
Security
Deniability
Computation Latency
Expression Complexity
Compute Platform Resources

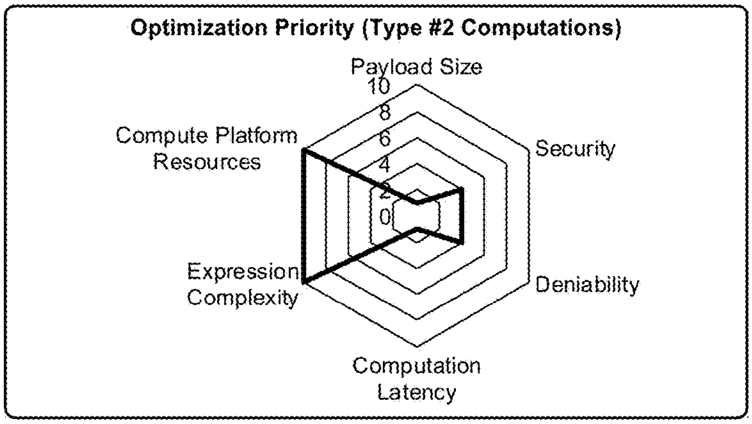

FIG. 6C
6D00
Optimization Priority (Type #3 Computations)
Payload Size
10
8
6
4
2
0
Security
Deniability
Computation Latency
Expression Complexity
Compute Platform Resources

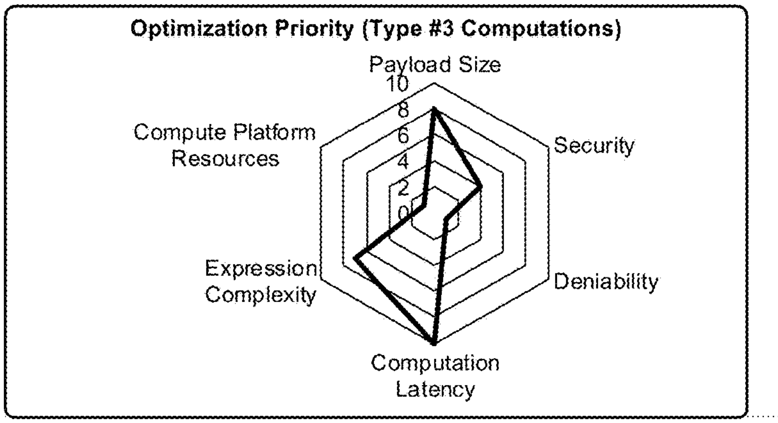

RESOURCE-EFFICIENT PRIVACY-PRESERVING TRANSACTIONS

RELATED APPLICATIONS

The present application is a continuation of, and claims the benefit of priority to U.S. patent application Ser. No. 17/135,917 titled "RESOURCE-EFFICIENT PRIVACY-PRESERVING ANALYTICS" filed on Dec. 28, 2020, which is a continuation-in-part of, and claims the benefit of priority to U.S. patent application Ser. No. 16/894,875 titled "RESOURCE-EFFICIENT PRIVACY-PRESERVING ANALYTICS" filed on Jun. 7, 2020 (now abandoned), and which is a continuation-in-part of, and claims the benefit of priority to U.S. patent application Ser. No. 16/537,523 titled "VERIFYING DATA ACCURACY IN PRIVACY-PRESERVING COMPUTATIONS" filed on Aug. 9, 2019 (now U.S. Pat. No. 10,878,950), which is a continuation-in-part of, and claims the benefit of priority to U.S. patent application Ser. No. 16/824,223 titled "DYNAMIC DATA PROTECTION" filed on Mar. 19, 2020 (now U.S. Pat. No. 11,461,499), which is a continuation of, and claims the benefit of priority to U.S. patent application Ser. No. 16/400,030 titled "DYNAMIC DATA PROTECTION" filed on Apr. 30, 2019 (now U.S. Pat. No. 10,635,837), all of which are hereby incorporated by reference in their entirety.

TECHNICAL FIELD

This disclosure relates to data analytics, and more particularly to techniques for negotiating resource-efficient privacy-preserving transactions between two or more computers.

BACKGROUND

The capabilities of the Internet continue to grow (e.g., greater geographic reach, higher and higher bandwidth, etc.). Overall, greater and greater quantities (and more and more types) of data are being transmitted over the Internet. Encryption techniques have long been applied to certain types of such data so as to allow two or more computers to securely communicate. Various public and private key, symmetric and asymmetric encryption protocols, and other encryption techniques have been deployed as standards (e.g., the secure socket layer (SSL) standard, the transport layer security (TLS) standard, etc.), and such encryption techniques have been applied in Internet communication protocols, for example, via the widely adopted secure hypertext transfer protocol (HTTPS).

The aforementioned secure hypertext transfer protocol may be secure by operation of encryption/decryption, however the overall security of shared information is limited by the extent that the parties trust each other to securely handle decrypted messages.

In recent times, there has emerged an awareness that any computing system, whether controlled by a trusted party or not, is vulnerable to cyber attacks. This awareness has brought to the fore a realization that anytime there exists a decrypted message on a computer connected to the Internet, that decrypted message is vulnerable to being stolen, altered, or otherwise exploited by cyber attackers.

In this age of ubiquitous online services, there exists a panoply of situations where certain types of sensitive data, and/or sensitive results from analysis of such sensitive data, is intended to never to be shared with any other party—whether trusted or not—in a decrypted fashion. If such sensitive data can only be accessed and changed by the person who provided or generated the data, then this greatly diminishes the possibility of malicious exploitation of the sensitive data. While never sharing such unencrypted sensitive data with any other party indeed greatly diminishes the possibility of malicious exploitation of the data, there is a significant problem. Namely, if other parties cannot see or compute on these data, it makes it impossible for two or more parties to communicate about sensitive subjects and, moreover, it also greatly diminishes the ability for the parties to analyze the data. What is desired in many of these situations are ways to perform analytics on encrypted data without ever decrypting the encrypted data.

To address this desire, much effort has gone into the development of homomorphic encryption. Homomorphic encryption (HE) allows computation on encrypted data. Application of homomorphic encryption to communications and computations allows for generation of encrypted results from encrypted inputs where, if the encrypted results were to be decrypted, the encrypted results would match the results of the same computations as if they had been performed on decrypted data (e.g., plaintext).

It has been well documented that the sheer amount of computational power needed for homomorphic encryption in combination with the sheer amount of communication bandwidth required to engage in multi-party sharing and encrypted computation over large amounts of sensitive data often far exceeds the computational power and communication capabilities of most computing devices (esp. handheld user devices). Strictly as one example, when using homomorphic encryption to facilitate an addition of two small integers (e.g., in the range of 0 to 9), both of which integers are meant to be exchanged only in mutually-agreed upon fully-homomorphic encrypted (FHE) forms, the digital payload to carry the two integers in their lattice-cryptographically protected form would exceed several tens of megabytes in size. Thus, the encrypted payload that would need to be transmitted to the party that is to analyze the data (in this case, by adding the two integers) is on the order of one million-fold or more larger than the two cleartext inputs.

Nevertheless, implementations of homomorphic encryption naïvely assume that all data to be exchanged between parties should be subjected to computationally—and/or bandwidth-intensive encryption techniques. Such naïve approaches are proven to have failed to achieve broad usage due at least to an unavailability of such huge computing resources. In an attempt to address these failures, various data re-representation techniques (e.g., tensor representation, tensor decomposition, etc.) have been combined with homomorphic encryption, however such re-representation techniques themselves have been shown to increase the overall computational load without significantly reducing the size of the payload, and thus, this attempt has also proven to have failed.

At the same time that researchers are developing techniques for using homomorphic encryption, use of computer techniques known as predictive analytics have gained traction. When observing exchanges between two computers involved in predictive analytics (e.g., in the insurance coverage field, the advertising field, the healthcare field, etc.) it emerges that not all data being exchanged are equally sensitive, and thus not all data being exchanged would need to be subject to the aforementioned computationally—and/or bandwidth-intensive encryption techniques. More specifically, while there may exist general privacy concerns (e.g., regarding medical data and/or other personally-identifiable data), and while there may exist general jurisdictional regulations (e.g., general data protection regulation (GDPR), HIPAA, etc.) not all such data need be subjected to expensive encryption techniques. In fact, certain "medical data," by themselves, does not need to be protected at all.

Consider a medical record for a patient that contains the field/value pair {"Thyroid Stimulus Hormone (TSH) Level", "7"}. In this case, neither the field name, "Thyroid Stimulus Hormone (TSH) Level" by itself, nor the value "7" by itself, are informational as to a medical condition, much less informational as to their correspondence to a particular patient. However, if the field and value are known to be associated as a pair and, further, if the pair is shared with another party and then associated with a patient, then the TSH level of that patient can be known by the other party. As such, there are opportunities for optimizing how sensitive data is handled.

Further, and specifically referring to optimizing privacy-preserving transactions between computers, any particular privacy-preserving transaction might be subject to corresponding limitations and/or requirements that vary significantly across a wide range of computing equipment capabilities and across a wide range of applications that rely on outcomes of privacy-preserving analytics.

Unfortunately, there are no known techniques or combination of techniques that allow interacting parties to negotiate locally optimal transactions while still enabling the ability to perform privacy-preserving analytics on sensitive data.

What is needed are ways to negotiate multi-party computer-to-computer transactions involving sensitive data.

SUMMARY

This summary is provided to introduce a selection of concepts that are further described elsewhere in the written description and in the figures. This summary is not intended to identify key features or essential features of the claimed subject matter, nor is it intended to limit the scope of the claimed subject matter. Moreover, the individual embodiments of this disclosure each have several innovative aspects, no single one of which is solely responsible for any particular desirable attribute or end result.

The present disclosure describes techniques used in systems, methods, and in computer program products for negotiating resource-efficient privacy-preserving transactions. These techniques advance the relevant technologies to address technological issues with legacy approaches. More specifically, the present disclosure describes techniques used in systems, methods, and in computer program products for negotiating resource-efficient privacy-preserving transactions over heterogenous data payloads with two or more data types. Certain embodiments are directed to technological solutions for preprocessing sensitive data items to match payload content volume with communication channel or processing capabilities.

The disclosed embodiments modify and improve over legacy approaches. In particular, the herein-disclosed techniques provide technical solutions that address the technical problems attendant to how to achieve high-performance privacy-preserving analytics even when one or more data elements and the analytics that will be performed on them are protected by homomorphic encryption. Such technical solutions involve specific implementations (i.e., data organization, data communication paths, module-to-module interrelationships, etc.) that relate to the software arts for improving computer functionality. Various applications of the herein-disclosed improvements in computer functionality serve to reduce demands for computer memory, reduce demands for computer processing power, reduce network bandwidth usage, and reduce demands for intercomponent communication. For example, when applying the herein-disclosed techniques, both memory usage and CPU cycles demanded are significantly reduced as compared to the memory usage and CPU cycles that would be needed but for practice of the herein-disclosed preprocessing of sensitive data items to match payload composition and size with communication channel or processing capabilities.

The ordered combination of steps of the embodiments serve in the context of practical applications that perform steps for preprocessing sensitive data items to match payload composition and size with communication channel or processing capabilities. As such, many of the disclosed techniques for preprocessing sensitive data items serve to match payload composition and size with communication channel or processing capabilities, which in turn overcomes long-standing yet heretofore unsolved technological problems associated with how to achieve high-performance privacy-preserving analytics even when one or more data elements and/or the analytics that will be performed on them are protected by homomorphic encryption.

Many of the herein-disclosed embodiments for preprocessing sensitive data items to match payload composition and size with communication channel or processing capabilities are technological solutions pertaining to technological problems that arise in the hardware and software arts that underlie privacy-preserving data exchange and analysis carried out over the public Internet. Aspects of the present disclosure achieve performance and other improvements in peripheral technical fields including, but not limited to, machine-machine interfaces and cyber threat avoidance.

Some embodiments include a sequence of instructions that are stored on a non-transitory computer readable medium. Such a sequence of instructions, when stored in memory and executed by one or more processors causes the one or more processors to perform a set of acts for preprocessing sensitive data items to match payload composition and size with communication channel or processing capabilities.

Some embodiments include the aforementioned sequence of instructions that are stored in a memory, which memory is interfaced to one or more processors such that the one or more processors can execute the sequence of instructions to cause the one or more processors to implement acts for preprocessing sensitive data items to match payload composition and size with communication channel or processing capabilities.

In various embodiments, any combinations of any of the above can be combined to perform any variation of acts for negotiating resource-efficient privacy-preserving transactions that are undertaken involving large amounts of mixed kinds of data. Many such combinations of aspects of the above elements are contemplated.

Further details of aspects, objectives, and advantages of the technological embodiments are described herein, and in the figures and claims.

BRIEF DESCRIPTION OF THE DRAWINGS

The drawings described below are for illustration purposes only. The drawings are not intended to limit the scope of the present disclosure.

FIG. 5B depicts a routine used in negotiating point-in-time payload reduction schemes when two computers are involved, according to some embodiments.

DETAILED DESCRIPTION

Figure 1A:
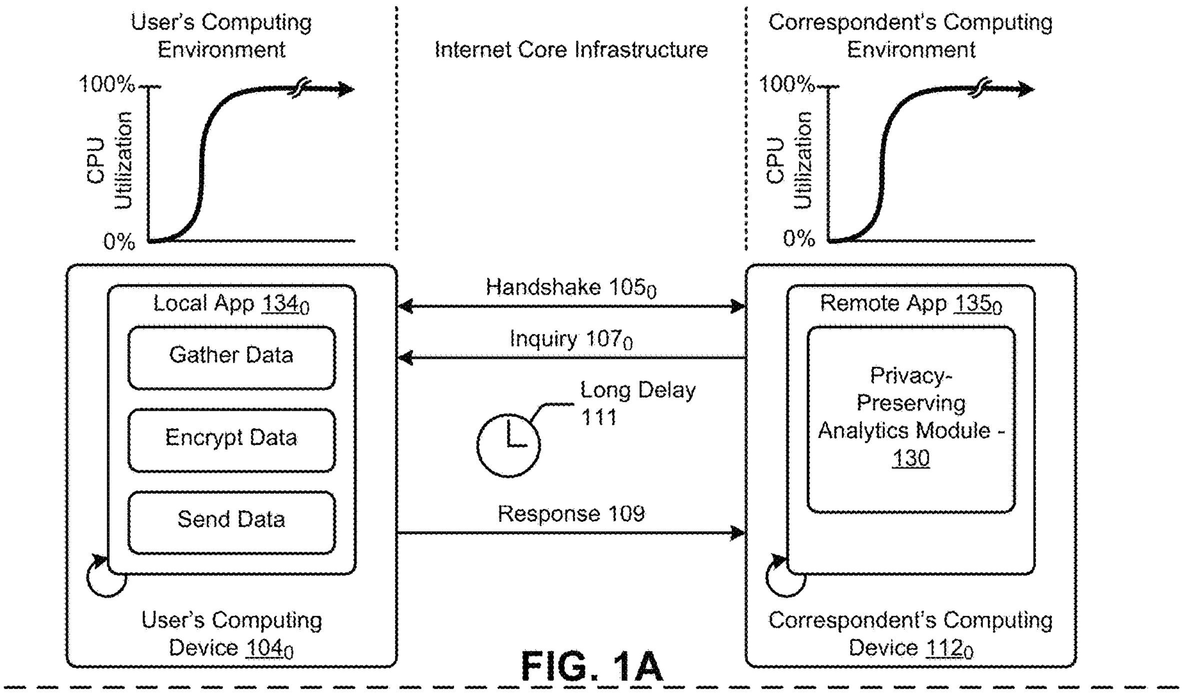
FIG. 1A depicts a computer-to-computer message exchange within an environment in which aspects of the present disclosure can be implemented.

Privacy-preserving analytic methods come in many forms, each of which forms can be modified for a particular purpose through selection and/or optimization of security and privacy settings (e.g., key lengths, specific cryptographic data handling techniques, data size reduction schemes, noise terms, etc.). Unfortunately, some or all of the techniques that support privacy-preserving analytics impose considerable computing overhead. This sets up the real-world scenario where factors such as (1) the computing power needed to generate keys, (2) the computing power needed to communicate payloads between computers, and (3) the computing power needed to perform the negotiated analytics might need to be considered in a trade-off analysis with respect to (4) the types of insights that could be extracted from the analytics and/or (5) the degree of cryptographic protection afforded to the subject data. In real-world applications that perform privacy-preserving analytics, there is no "one-size-fits-all" grouping of predetermined security and privacy settings.

Rather, in real-time, a computer with subject data (hereinafter, the "source device") communicates with one or more computers that have available computing resources (hereinafter the "worker devices"). The computers exchange information between themselves and negotiate an optimal combination (hereinafter, a "privacy regime") that specifies data reduction schemes, encryption techniques, and security settings as well as other aspects pertaining to the privacy regime. The source device then comports to the negotiated privacy regime to form heterogeneous, multi-segment data payloads, which are sent to the worker devices. In typical cases, at least one data segment of communicated data payloads are protected by homomorphic encryption or secure multiparty computation (SMC). One or more of the other segments may be encrypted using other algorithms, and/or one or more of the other segments may be generated by varying the security-relevant parameters of the invoked encryption scheme or schemes.

A particular privacy regime is negotiated based on one or more of available communication bandwidth, network latency, source and worker processing resources, degree of accuracy sought by the owner of the data, degree of privacy sought by the data owner, etc. For example, in the hypothetical case of having unlimited computing resources, the interacting computers may negotiate between themselves to apply fully homomorphic encryption to large portions of the data payload. As another example, if the source device is compute-power constrained such that the source device struggles with key generation (e.g., generation of private and multiplication and rotation keys), the computers may negotiate among themselves to reduce the number of data elements protected by highly compute-intensive encryption (e.g., homomorphic encryption), and may negotiate among themselves to agree on use of less compute-intensive encryption for portions of the data payload, while still achieving sought-after accuracy and privacy.

As disclosed hereunder, aspects of the present disclosure solve problems associated with using computer systems to achieve high-performance multi-party privacy-preserving analytics even when some data elements and their analytics employ homomorphic encryption. Some embodiments are directed to approaches for negotiating how to preprocess sensitive data items to match payload composition and size with communication channel bandwidth and/or processing capabilities that are determined to be available at the time of payload exchange. Some of the accompanying figures and discussions herein present example environments, systems, methods, and computer program products for negotiating resource-efficient privacy-preserving transactions that involve heterogeneous data payloads.

Overview

Homomorphic encryption (HE) can be used for privacy-preserving cloud storage and computation. Use of HE allows sensitive user data to be first encrypted and then transmitted to other parties (e.g., parties often referred to as worker devices or "cloud workers"), for processing—while both the sensitive user data as well as the results of corresponding analysis are always encrypted for all operations.

Privacy regulations are common in the healthcare ecosystem. Homomorphic encryption can be used to enable healthcare services by removing privacy barriers that might otherwise inhibit data sharing. For example, predictive analytics in healthcare can be difficult to apply due to medical data privacy concerns, however if the predictive analytics service provider can operate on encrypted patient data, many privacy concerns can be diminished or eliminated.

Further, there are other industries where the privacy concerns are bidirectional. For example, a vehicle operator might want a quote from an insurance carrier that offers the best insurance rate, yet the vehicle operator might want to do so without initially divulging the exact details of the vehicle and/or the vehicle operator's personally-identifiable information (PII). At the same time, the insurance carrier might want to collect non-PII information about the operator, yet without divulging the exact nature of the data being collected and/or how it is being used. To do so often demands application of fully homomorphic encryption techniques such that neither the operator nor anyone else other than the insurance carrier can know the nature of the data being collected nor the nature of operations, nor can anyone else other than the insurance carrier know the results of the operations on the data.

Fully Homomorphic Cryptosystems

A cryptosystem that supports arbitrary computation on ciphertexts is known as fully homomorphic encryption (FHE). Such a scheme enables construction of programs—for any desirable functionality—that can be run on encrypted inputs to produce an encryption of the result. Since such a program need never decrypt its inputs, it can be run by an untrusted party without revealing its inputs nor its internal state. Unfortunately, it often happens that the quantity of data that needs to be exchanged between untrusted parties explodes when using FHE, making it impractical in most situations.

Preprocessing of Sensitive Data Before Applying FHE

Consider a scenario where a patient has a sonogram image of her uterus, and the question to be answered by an untrusted party is, "Based on this sonogram, am I pregnant?" One way to get the answer is for the patient to send an encrypted sonogram image and a decryption key to a trusted party, and then ask the trusted party to render the answer from an analysis of the image. However, this method has the undesired property that the image is decrypted by a party other than the patient. Another way to get the answer is for the patient and an untrusted third party to use FHE. In that case, the patient sends an encrypted sonogram image—without a decryption key—to the untrusted third party and asks the untrusted third party to send back an encrypted result with the answer to the question, "Based on this sonogram, am I pregnant?"

In this scenario, the untrusted third party never holds the sonogram image in decrypted form, and the untrusted third party never holds the results of analysis of the sonogram in decrypted form, thus the patient's pregnancy status is not known by any entity other than the patient herself, since she is the only one to hold the private (decryption) key for the sonogram image and the analysis results.

Unfortunately, the amount of data of the encrypted sonogram image makes it impractical to carry out this kind of computerized analysis using even the most modern computers and even the most modern network infrastructure. However, if the sonogram image where to be preprocessed such that, for example, only the portion of the sonogram image that is actually dispositive as to the pregnancy status of the patient is isolated before being encrypted and sent to the untrusted third party, then the analysis moves from being impractical to being at least possibly practical.

Further details pertaining to this technological problem as well as many practical implementations of technological solutions to the technological problem are shown and described as pertains to the figures.

Definitions and Use of Figures

Some of the terms used in this description are defined below for easy reference. The presented terms and their respective definitions are not rigidly restricted to these definitions—a term may be further defined by the term's use within this disclosure. The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application and the appended claims, the term "or" is intended to mean an inclusive "or" rather than an exclusive "or". That is, unless specified otherwise, or is clear from the context, "X employs A or B" is intended to mean any of the natural inclusive permutations. That is, if X employs A, X employs B, or X employs both A and B, then "X employs A or B" is satisfied under any of the foregoing instances. As used herein, at least one of A or B means at least one of A, or at least one of B, or at least one of both A and B. In other words, this phrase is disjunctive. The articles "a" and "an" as used in this application and the appended claims should generally be construed to mean "one or more" unless specified otherwise or is clear from the context to be directed to a singular form.

Various embodiments are described herein with reference to the figures. It should be noted that the figures are not necessarily drawn to scale, and that elements of similar structures or functions are sometimes represented by like reference characters throughout the figures. It should also be noted that the figures are only intended to facilitate the description of the disclosed embodiments—they are not representative of an exhaustive treatment of all possible embodiments, and they are not intended to impute any limitation as to the scope of the claims. In addition, an illustrated embodiment need not portray all aspects or advantages of usage in any particular environment.

An aspect or an advantage described in conjunction with a particular embodiment is not necessarily limited to that embodiment and can be practiced in any other embodiments even if not so illustrated. References throughout this specification to "some embodiments" or "other embodiments" refer to a particular feature, structure, material or characteristic described in connection with the embodiments as being included in at least one embodiment. Thus, the appearance of the phrases "in some embodiments" or "in other embodiments" in various places throughout this specification are not necessarily referring to the same embodiment or embodiments. The disclosed embodiments are not intended to be limiting of the claims.

Descriptions of Example Embodiments

FIG. 1A depicts a computer-to-computer message exchange 1A00 within an environment in which aspects of the present disclosure can be implemented. The figure is being presented to illustrate the need to address the need to achieve high-performance multi-party privacy-preserving analytics even when some analytics require homomorphic encryption. The representative scenario depicts a user computer (e.g., user's computing device $\mathbf{104}_0$) that is in communication with another computer (e.g., correspondent's computing device $\mathbf{112}_0$) using messaging over the Internet.

As shown, an edge-device software application (e.g., local app $\mathbf{134}_0$) is in communication with another software application (e.g., remote app $\mathbf{135}_0$) using Internet messaging. Specifically, the two applications engage in a communication preamble (e.g., handshake $\mathbf{105}_0$) followed by an inquiry $\mathbf{107}_0$ by the remote app $\mathbf{135}_0$ and a response 109 from the local app $\mathbf{134}_0$. The remote app is configured to be able to perform analytics through use of the privacy-preserving analytics module 130; however, there is a long delay 111 between the inquiry $\mathbf{107}_0$ and the response 109. This long delay is because the amount of data to be communicated over the Internet between computers becomes enormous when homomorphic encryption is naively employed. For example, a single medical image with a typical size of 10 MB would balloon into a 10 TB-sized file, which cannot be loaded into the memory of any but the most powerful supercomputers, even then would typically be needed to be transferred from one computer to another by physically shipping hard-drives through the mail. Both repercussions—that is, the inability to load the FHE image file into memory and the need to transfer the data through physical shipment of hard drives to supercomputer datacenters effectively precludes naïve use of FHE in this type of application. Moreover, although conventional techniques might be employed by the edge device to gather and send data, the acts involved to encrypt data when homomorphic encryption is employed demands 100% CPU utilization at the edge device. Similarly, when the privacy-preserving analytics module 130 does finally receive a complete response to the inquiry (e.g., via an encrypted message as encrypted by the edge device), the CPU of the computer that hosts the privacy-preserving analytics module 130 also demands 100% CPU utilization to process the response.

The combination of huge amounts of CPU resources demanded for processing data that has been encrypted using homomorphic encryption, together with the long delay between an inquiry and communication of a complete response to the inquiry, frames the problem to be solved. This problem can be ameliorated by applying one or more of the herein-disclosed techniques. Some or all of the herein-disclosed techniques for preprocessing sensitive data items to match payload content volume with communication channel or processing capabilities can be employed to achieve performance improvement in any environment or configuration of computers.

Referring again to the term "payload content volume," and more specifically to the term "payload", as used herein the term "payload" refers to data exchanged by computers, whether by transmission (e.g., over the Internet) or by operation of shared access to a commonly-accessible storage location (e.g., a shared memory, a shared hard drive, etc.). As one example, when computers interact, they share data in the form of predefined digital packets or payloads, each with elements drawn from, for example, a payload type designator, a payload checksum, a hash value, one or more other integrity check elements, and one or more data elements. Each of the foregoing elements can be secured and/or shared in a computer-to-computer message exchange and/or computed upon in a multitude of ways, some of which are disclosed herein, and some of which are shown and described as pertains to FIG. 1B, which is now briefly discussed.

Figure 1B:
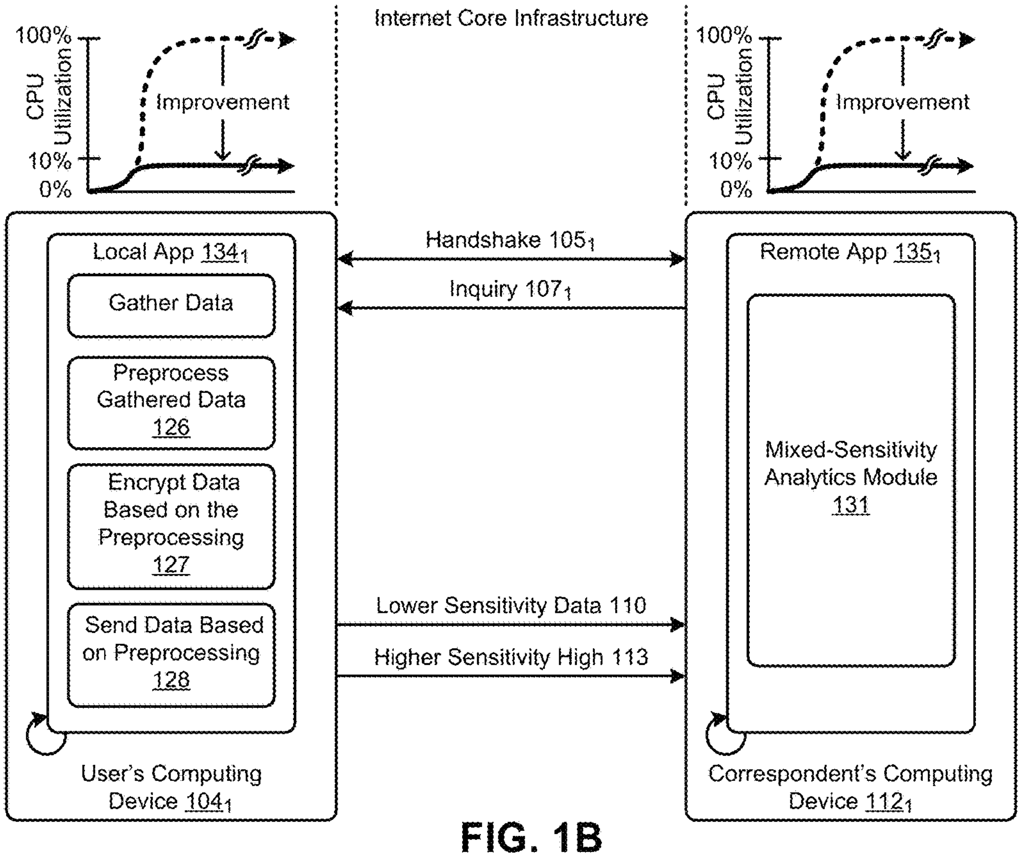
FIG. 1B depicts a computer-to-computer message exchange in which implementation of aspects of the present disclosure achieve computer resource utilization improvements, according to some embodiments.

FIG. 1B depicts a computer-to-computer message exchange 1B00 in which implementation of aspects of the present disclosure achieve computer resource utilization improvements. FIG. 1B illustrates aspects pertaining to preprocessing sensitive data items to match payload content volume with communication channel or processing capabilities. Specifically, the figure is being presented with respect to its contribution to addressing the problem of how to achieve high-performance multi-party privacy-preserving analytics even when some analytics require homomorphic encryption. As depicted in FIG. 1B, the steps and/or operations at the user's computing device $\mathbf{104}_1$ are associated with steps to gather data, encrypt data, and send data; however, and as shown, the configuration of the local app $\mathbf{134}_1$ hosted by the user's computing device $\mathbf{104}_1$ includes steps to preprocess gathered data (e.g., preprocessing module 126) as well as steps to encrypt the preprocessed data based on the results of preprocessing.

The local app $\mathbf{134}_1$ is able to carry out a handshake $\mathbf{105}_1$ and is able to respond to inquiry $\mathbf{107}_1$; however, as distinguished from the configuration of FIG. 1A, the configuration of FIG. 1B is able to send data to the correspondent's computing device $\mathbf{112}_1$ without incurring a long delay and without demanding 100% of the available CPU cycles. This is because the steps to preprocess gathered data (e.g., preprocessing module 126) and the steps to encrypt the preprocessed data—based on the results of preprocessing and/or based on characteristics of any of the then-current communication channels-serve to divide the gathered data into lower sensitivity data 110 and higher sensitivity data 113, such that the very expensive homomorphic encryption algorithms are applied only to the higher sensitivity data 113, whereas the lower sensitivity data 110 is processed (e.g., via encryption processing module 127) using a less expensive encryption algorithm and sent (e.g., via sending module 128) using less communication channel bandwidth.

This smaller amount of data being subjected to encryption using very expensive homomorphic encryption algorithms also means that the analytics performed at the remote app $135_1$ do not demand 100% of the available CPU cycles. This is because the mixed-sensitivity analytics module 131 is configured to perform different privacy-preserving analytics over data of mixed sensitivity and, as such, only some portion of the data exchanged between the computers is subjected to the very expensive homomorphic encryption algorithms.

The foregoing discussion of FIG. 1B introduces the concept of preprocessing gathered data to reduce the amount of computer resources used. An example preprocessing system for preprocessing gathered data, as well as various example techniques for how to preprocess gathered data, are disclosed in detail as follows.

Figure 2A:
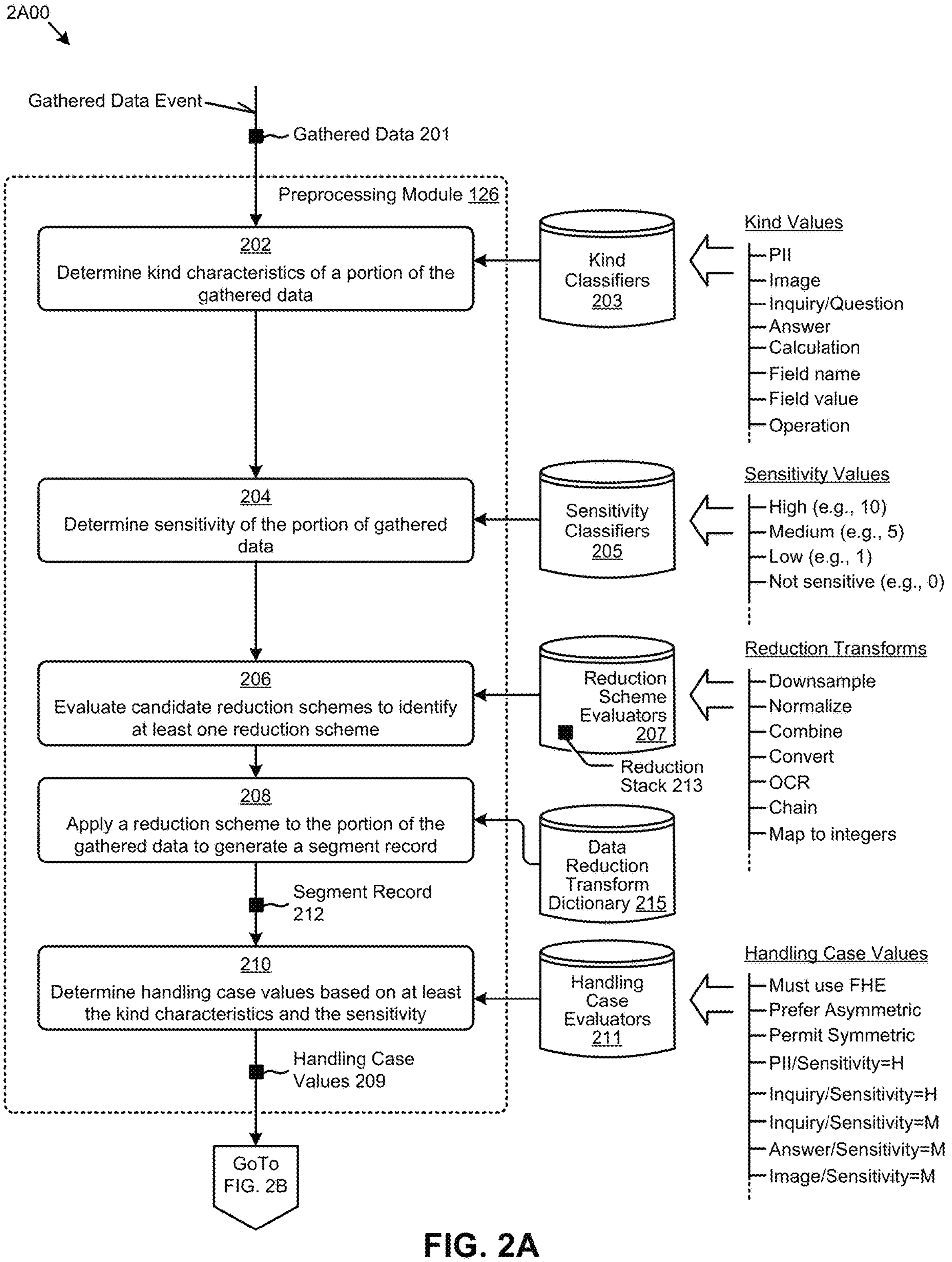
FIG. 2A illustrates a preprocessing system as used to achieve computer resource utilization improvements when sharing large amounts of sensitive data, according to some embodiments.

FIG. 2A illustrates a preprocessing system 2A00 as used to achieve computer resource utilization improvements when sharing large amounts of sensitive data. As an option, one or more variations of preprocessing system 2A00 or any aspect thereof may be implemented in the context of the architecture and functionality of the embodiments described herein. The preprocessing system 2A00 or any aspect thereof may be implemented in any environment.

FIG. 2A illustrates aspects pertaining to preprocessing sensitive data items to match payload content volume with communication channel or processing capabilities. Specifically, the figure is being presented with respect to its contribution to addressing the problem of how to reduce the amount of data to be subjected to multi-party privacy-preserving analytics. The shown flow receives notification of availability of gathered data, then preprocesses the gathered data to determine how to handle a particular portion of gathered data. During the performance of steps carried out by preprocessing module 126, a segment record is generated, and various fields of the segment record are populated with corresponding field values. These field values are used by downstream processing. Strictly as one example, if a particular portion of the gathered data is deemed to contain personally-identifiable information (PII) then it would be marked as such (e.g., “kind”=“PII”), and that determination might be used in downstream processing to determine a degree of sensitivity (e.g., “sensitivity”=“High” or “sensitivity”=“10”), which in turn might determine or influence how that portion of the gathered data is handled.

As shown, processing of gathered data 201 commences upon an event that corresponds to data that has been gathered in response to an inquiry (e.g., inquiry $107_1$ of FIG. 1B). The event serves to invoke preprocessing module 126. Various types of classifiers are used by submodules of preprocessing module 126. In the example shown, a portion of the gathered data is selected and then subjected to the foregoing classifiers. More specifically, and as shown, various kind characteristics are determined (step 202) by applying one or more kind classifiers 203 to any portions of the gathered data. The kind characteristics can be codified as numbers. Any given portion of gathered data can be classified by multiple classifiers, and as such any given portion of gathered data might be associated with multiple kind values that, in turn, can be codified as “kind”={“PII”, “Answer”}, or “kind”={“1”, “3”}, etc.

Once a particular portion of gathered data has been classified, a determination is made as to the sensitivity of the particular portion of gathered data (step 204). Any number of sensitivity classifiers 205 may be applied to a portion of the gathered data. In some cases, the kind of data is considered when determining a sensitivity. Any sensitivity classifier can classify to a particular sensitivity level or, in some cases, a sensitivity classifier can classify to a particular sensitivity level range. In some cases, there might not be any sensitivity classifiers that can determine a sensitivity value to any particular degree of statistical confidence and, in such cases, a default sensitivity value is assigned to the considered portion of the gathered data.

Having made a determination as to the kind and sensitivity of the subject portion of gathered data, any number of data reduction schemes (e.g., as depicted by reduction stack 213) might be evaluated (at step 206) for application over the subject portion of data (at step 208) so as to generate a segment record 212. Candidate data reduction schemes or data reduction paths may be codified into a dictionary (e.g., data reduction transform dictionary 215). Each entry in such a dictionary describes one or more steps or one or more series of steps that apply a transformation to a subject portion of gathered data such that the result of the transformation is either smaller in size (e.g., fewer bits or bytes), or in some other way less expensive to operate on when encrypting, and/or or in some way less expensive to operate on when performing operations on encrypted data. Strictly as one example, if a floating-point multiplication (or other expensive floating-point operation) were to be performed in the blind over two floating-point numbers, but it is observed that the floating-point numbers can be reduced to fixed-point numbers and operated on using fixed-point multiplication (or other less expensive fixed-point operation), and if the loss of precision were within some given tolerance, then a data reduction scheme to transform the floating-point numbers into fixed-point numbers might be deemed to be a good candidate.

For example, assessment of cardiovascular risk can involve consideration of a person’s BMI (body mass index). A person’s BMI is often represented as a floating-point number such as 24.370401. However, assessment of cardiovascular risk is simply based on whether a person’s BMI is greater than 25 (for a medium risk level assessment), or greater than 30 (for a higher risk level assessment). A simple but highly effective preprocessing scheme would therefore map a floating-point input like 24.370401 to one of the integers from among {‘0’, ‘1’, or ‘2’} to denote a BMI of <25 (e.g., using integer ‘0’), or to denote a BMI between 25 and 30 (e.g., using integer ‘1’), or to denote a BMI of >30 (e.g., using integer ‘2’). Such a preprocessing technique significantly broadens the types of privacy-preserving computation that can be applied to the data, at least in that this preprocessing technique serves to significantly reduce data payload sizes, while incurring no impact on the quality of the risk assessment as computed by an untrusted cloud worker.

The foregoing reduction by recoding floating-point numbers to fixed-point representations is merely one example. Other transforms are possible, and any one or more reduction scheme evaluators 207 might be employed singly and/or in combination to result in a determined data reduction scheme. A data reduction scheme defines an ordered series of reduction transforms, which can be any series of reduction transforms regardless of where the reduction is performed. As another example, consider that an insurance carrier might want to know whether an insured vehicle is parked at the same location every night. For purposes of reducing the amount of data sent/received pertaining to the moment-by-moment location of the vehicle, rather than transmitting the location of the vehicle moment-by-moment, or even every time it is parked, an algorithm can be run locally (e.g., by the vehicle’s computer or on a proxy device such as a smart phone) so as to detect a final parked location for the day. In this example, only the final parked location for the day needs to be encrypted. In a still further example of a data reduction technique, perhaps only the binary (e.g., single bit, "Yes or No") answer to the question, "Yes/No: Is this vehicle parked at the same location as yesterday?" is needed.

A sample set of image transforms comprising "downsampling" and "edge detection" as well as a sample set of "normalizing" and "combining" examples are shown. Other transforms are possible, some of which are shown and described as pertains to FIG. 5A and FIG. 5B.

At some point during processing within the preprocessing module 126, a segment record 212 is formed and at least partially populated with values (e.g., kind values, sensitivity values, etc.). The segment record 212 comprises a variable length field to hold an encrypted payload. The contents of the variable length field to hold an encrypted payload can change as conditions change (e.g., CPU availability, CPU characteristics, bandwidth availability, bandwidth characteristics, etc.). To accommodate a rapid response to changing conditions, preprocessing module 126 (e.g., at step 210) can use specialized classifiers (e.g., handling case evaluators 211) to assign a handling case value 209 based on the contents of subject segment record 212. Step 210 further serves to codify any number of handling case values 209 into an array or other multi-valued set within a subject segment record. For example, if the kind value for a particular portion of gathered data is a person's name (and deemed to be "PII", which would suggest a higher sensitivity), and a determined data reduction scheme might be to hash the person's name before sending (which would suggest a lower sensitivity), then it might be possible to handle the person's name using either FHE or handle the hashed value of the person's name using a lower cost encryption or obfuscation scheme. At the time of actual transmission, the Internet channel can be measured, and based on the measurement, the encryption or obfuscation handling case can be dynamically selected.

Once the segment record 212 has been at least partially populated with at least one of the handling case values 209, corresponding encryption algorithm candidates are codified into the segment record. One technique for doing so is shown and described as pertains to the encryption candidate assignment module of FIG. 2B.

Figure 2B:
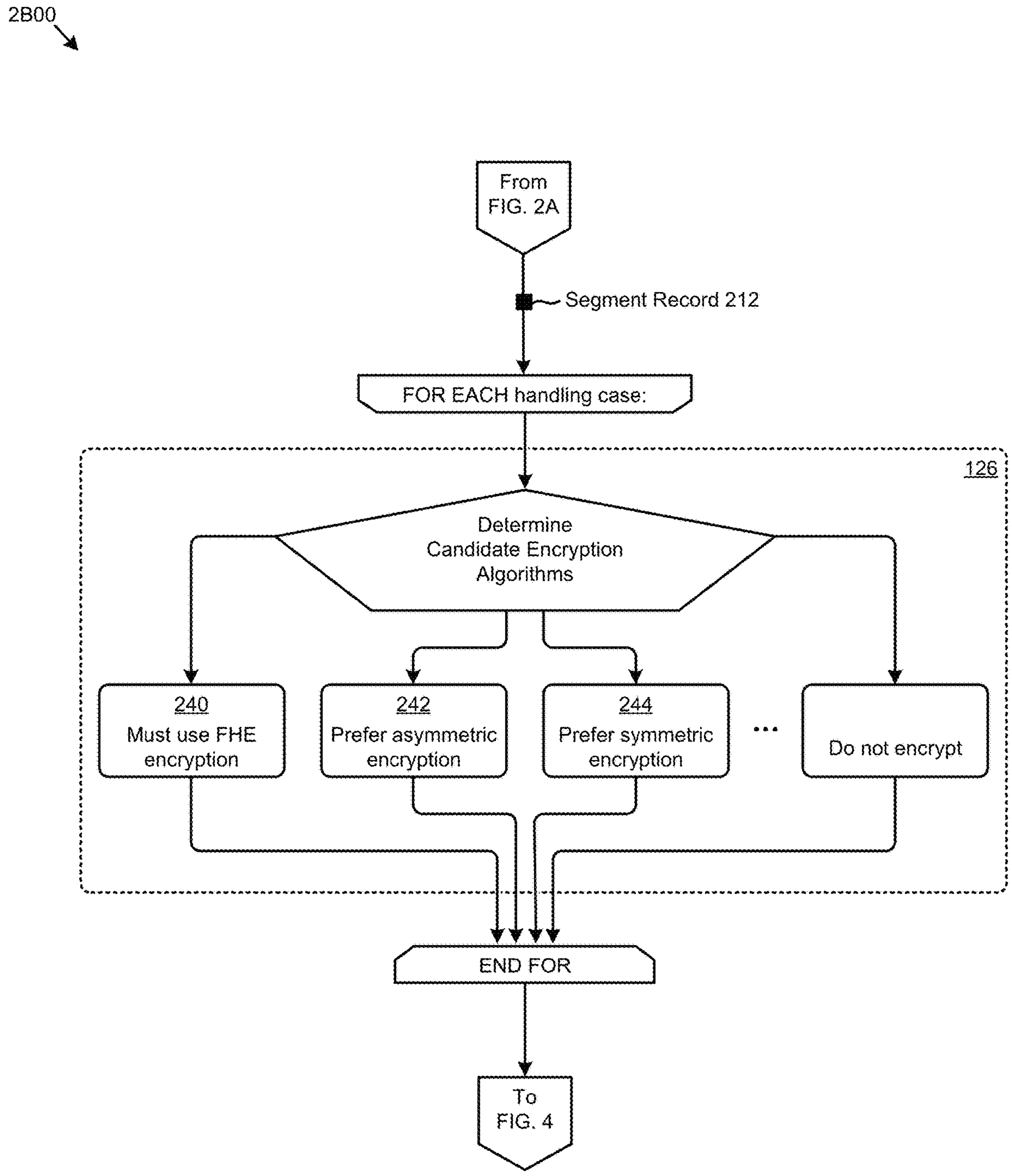
FIG. 2B depicts an encryption candidate assignment module as used to optimize computer resource utilization when dealing with large amounts of sensitive data, according to some embodiments.

FIG. 2B depicts an encryption candidate assignment module 2B00 as used to optimize computer resource utilization when dealing with large amounts of sensitive data. As an option, one or more variations of encryption candidate assignment module 2B00 or any aspect thereof may be implemented in the context of the architecture and functionality of the embodiments described herein. The encryption candidate assignment module 2B00 or any aspect thereof may be implemented in any environment.

The encryption candidate assignment module 2B00 serves to assign one or more candidate encryption algorithms to a particular segment record 212. In some cases, the handling case requires a particular encryption algorithm to be applied, whereas in other cases multiple different encryption algorithms might satisfy combinations of privacy requirements and CPU and/or bandwidth availability. Multiple different encryption algorithms might be designated in an array or other multi-valued set within a subject segment record. Furthermore, and as earlier indicated, there may be any number of handling case values 209 that are codified into an array or other multi-valued set within a subject segment record. As such, certain steps within the preprocessing module 126 can be performed in a loop so as to determine any number of candidate encryption algorithms that apply to a given segment record. For segment records that are coded with a plurality of candidate encryption algorithms (e.g., in the aforementioned array or another multi-valued set within a subject segment record), the determination of which candidate encryption algorithm can be employed before sending can be made at the time the subject segment record is ready for transmission.

The discrete handling cases shown in FIG. 2B (e.g., must use FHE encryption 240, prefer asymmetric encryption 242, prefer symmetric encryption 244, etc.) as well as the handling cases of Table 1 are presented here merely as examples. Furthermore, paired handling cases (e.g., "PII and Sensitivity=H," "Answer and Sensitivity-M," etc.) are also merely examples, and many other possibilities exist. The foregoing handling cases, whether presented as a discrete handling case, or whether presented as paired handling cases, are presented here merely as illustrations; many other possibilities exist.

TABLE 1

Example handling cases

| Short Name | Description |
|---|---|
| Must use FHE | Some exchanges may be explicitly negotiated to be handled using FHE only. This can occur, for example, when a correspondent does not want others to know the nature of the operation to be performed and/or when a correspondent does not want others to know the nature of the data over which the operation is performed. |
| Prefer Asymmetric | This case indicates that asymmetric encryption is preferred or required such as when no secure channel yet exists for key exchange. |
| Prefer Symmetric | This case indicates that symmetric encryption is permissible based on existence of a secure channel for key exchange. |
| PII and High Sensitivity Combination | This case indicates that the exchange includes personally identifiable information that is deemed to be of high sensitivity. A segment record that is marked to correspond to a combination of "PII and High Sensitivity" would normally be sent only when there is sufficient bandwidth to transmit the segment using homomorphic encryption. |
| Inquiry and High Sensitivity | This case indicates that even the inquiry itself is highly sensitive. |
| Inquiry and Low Sensitivity | This case indicates that the inquiry is by itself not very sensitive and does not need powerful encryption, thus it can be transmitted even during periods of low CPU and/or low bandwidth availability. |

The contents of segment records can be stored in a segment record data structure prior to being subjected to transmission as an Internet protocol packet over a communication channel. Possible embodiments and uses of a segment record data structure and Internet protocol packet are shown and described as pertains to FIG. 3A and FIG. 3B.

Figure 3A:
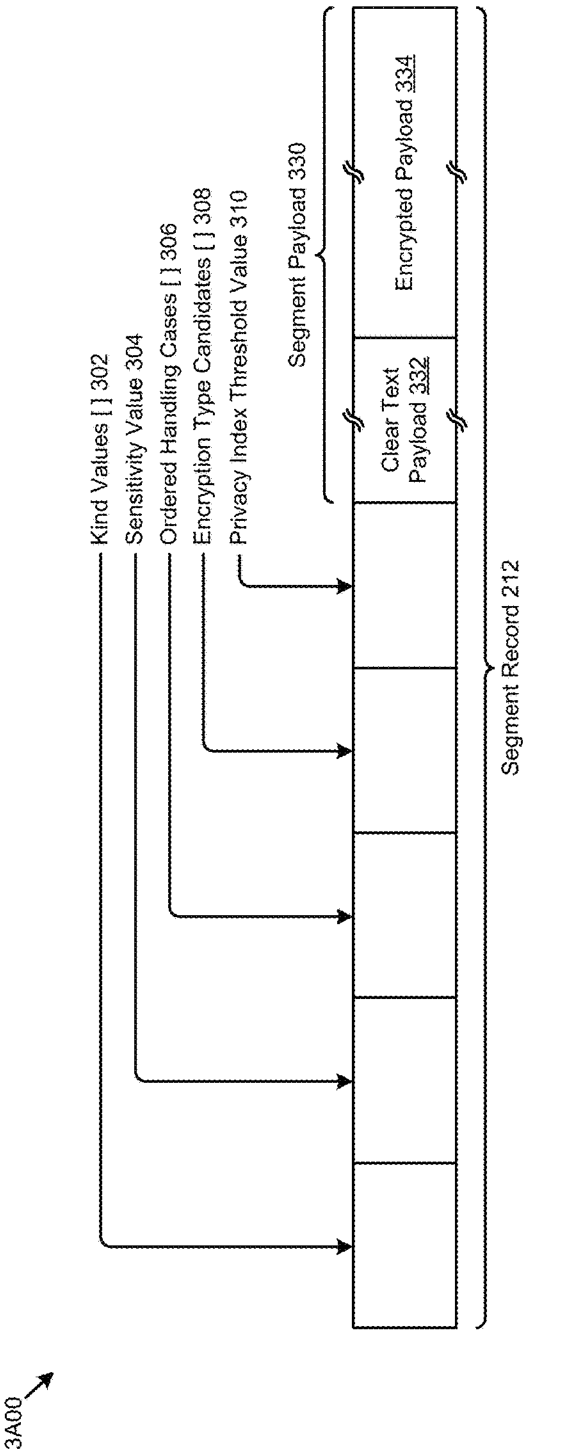
FIG. 3A is a diagram describing a segment record data structure as used in carrying out resource-efficient privacy-preserving transactions, according to some embodiments.

FIG. 3A is a diagram describing a segment record data structure 3A00 as used in carrying out resource-efficient privacy-preserving transactions. As an option, one or more variations of segment record data structure 3A00 or any aspect thereof may be implemented in the context of the architecture and functionality of the embodiments described herein. The segment record data structure 3A00 or any aspect thereof may be implemented in any environment.

The shown segment record data structure 3A00 includes flags and a variable length segment payload 330. The flags include a set of kind values 302, a sensitivity value 304, a set of ordered handling cases 306, a set of encryption type candidates 308, and a privacy index threshold value 310, any of which may correspond to the data within the encrypted payload 334. The shown segment record data structure 3A00 includes a variable length range for any clear text payload 332. The semantics of the foregoing flags correspond to the foregoing descriptions. A sender and a receiver can negotiate use of flags prior to transmission of any segment records. More specifically, during a communication preamble, or during some portion of an Internet exchange handshake, the sender and receiver can agree on which flags are to be sent, and in which format. Accordingly, when the aforementioned flags are communicated between computers, both the sending computer and the receiving computer agree on the representation and meaning of the flags.

The flags can be transmitted in any manner. For example, the flags can be transmitted separate from the encrypted payload to which the flags correspond, or the flags can be transmitted in the same packet as the encrypted payload. The latter case of transmitting flags in the same packet as the encrypted payload is shown and described as pertains to FIG. 3B.

Figure 3B:
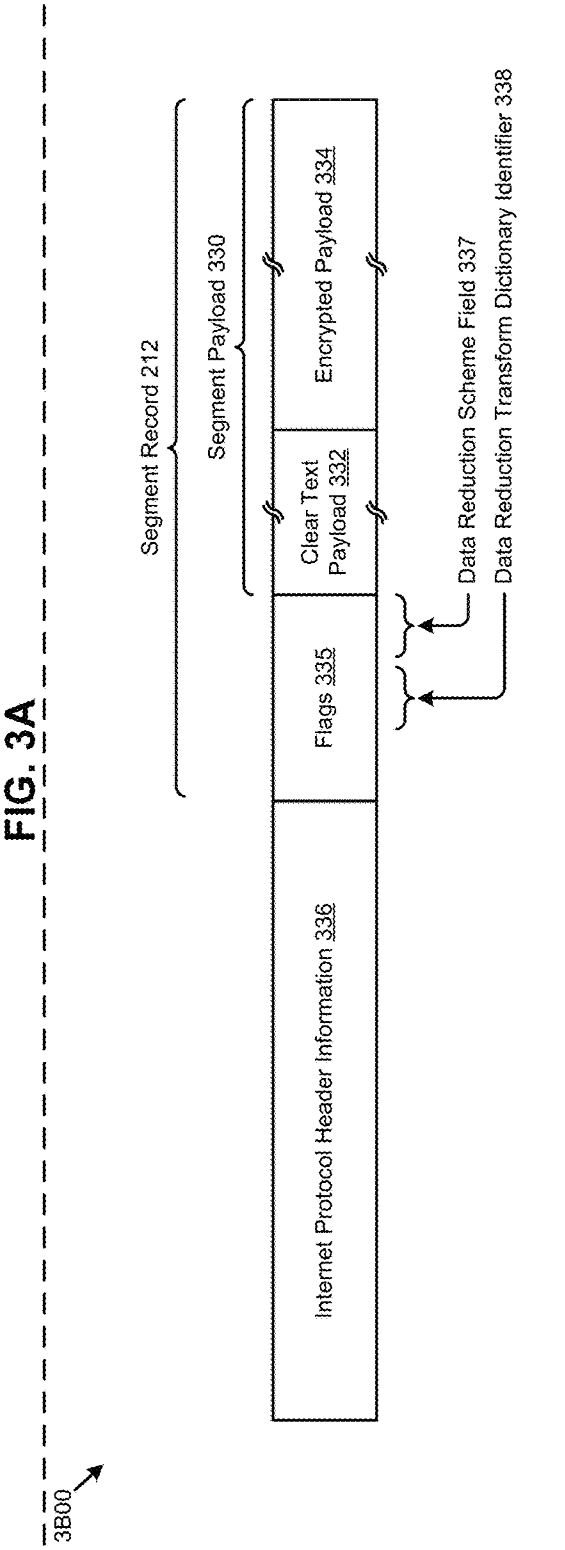
FIG. 3B is a diagram showing an encrypted payload within an Internet protocol packet as used when communicating between two computers involved in carrying out negotiated resource-efficient privacy-preserving transactions, according to some embodiments.

FIG. 3B is a diagram showing an encrypted payload within an Internet protocol packet 3B00 as used when communicating between two computers involved in carrying out negotiated resource-efficient privacy-preserving transactions. As an option, one or more variations of Internet protocol packet 3B00 or any aspect thereof may be implemented in the context of the architecture and functionality of the embodiments described herein. The Internet protocol packet 3B00 or any aspect thereof may be used in any computer-to-computer communication environment.

The shown Internet protocol packet 3B00 comprises Internet protocol header information 336, to which is appended any number of flags 335, a clear text payload 332, and an encrypted payload 334. In some cases, and as shown, the segment record 212 in its entirety is appended to the Internet protocol header information 336.

In some embodiments, the foregoing flags 335 may include a multi-bit field that contains a reduction path description that codifies information pertaining to any one or more specific data reduction transforms and/or any combinations or series of reduction transforms. In some cases, the foregoing flags 335 may further include a multi-bit field that contains a designation of a data reduction transform dictionary. More specifically, and as shown, the foregoing flags 335 may include a first field to hold a data reduction scheme and the foregoing flags 335 may include a second field to hold a data reduction transform dictionary identifier 338. The specific data reduction scheme specified in the first field refers to at least one possible transform path given by the data reduction transform dictionary of the second field. Example embodiments involving a combination or a series of reduction transforms and embodiments involving use of a data reduction transform dictionary are further described hereunder.

The determination of any particular feasible or optimal data reduction scheme may be dependent, at least in part, on the communication channels used by two computers involved in data representation-related and encryption-related negotiations. One particular channel-driven technique is shown and described as pertains to FIG. 4A.

Figure 4A:
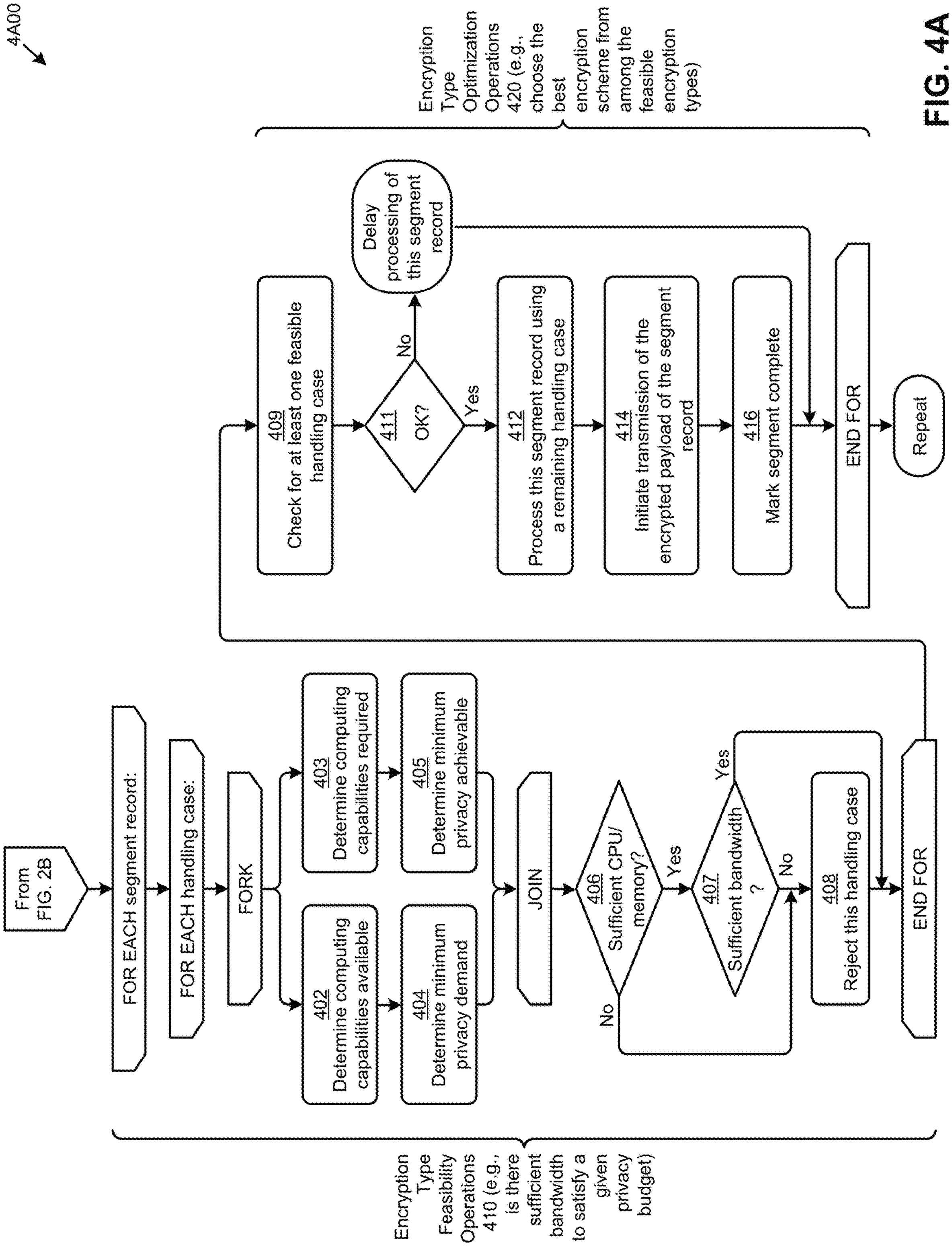
FIG. 4A depicts a channel-driven encryption technique as used to identify feasible and optimal reduction scheme candidates when communicating segment records between two computers involved in negotiating resource-efficient privacy-preserving transactions, according to some embodiments.

FIG. 4A depicts a channel-driven encryption technique 4A00 as used to identify feasible and optimal data reduction scheme candidates when communicating segment records between two computers involved in negotiating resource-efficient privacy-preserving transactions. As an option, one or more variations of channel-driven encryption technique 4A00 or any aspect thereof may be implemented in the context of the architecture and functionality of the embodiments described herein. The channel-driven encryption technique 4A00 or any aspect thereof may be implemented in any environment.

FIG. 4A illustrates aspects pertaining to preprocessing sensitive data items to match payload content volume with communication channel or processing capabilities. Specifically, the figure is being presented with respect to its contribution to addressing the problem of how to achieve high-performance multi-party privacy-preserving analytics even when some analytics require homomorphic encryption and even when the communication channel conditions may vary over time.

The channel-driven encryption technique commences at some moment after preprocessing has completed. More specifically, the shown channel-driven encryption technique commences at some moment after at least one segment record has been at least partially populated. The shown flow includes a FOR EACH loop that operates over each segment record that is available and has been populated with at least one handling case. The shown flow also includes a FOR EACH loop that operates over the handling cases that have been determined for this segment record. The technique includes encryption type feasibility operations 410 that are associated with a dynamic determination of feasibility of a particular handling case as well as encryption type optimization operations 420 that are associated with a dynamic determination of a then-optimal encryption algorithm.

The encryption type feasibility operations 410 include several assessments that are concomitantly carried out (e.g., within the FORK/JOIN block). At code block 402, tests to determine the then-current computing capabilities available is initiated. The tests may involve local determination of CPU and memory headroom at the user's computing device, and/or the tests may involve querying the correspondent's computing device to determine CPU and memory headroom at the correspondent's device. The tests may also involve determination as to the condition of the channel between the user's computing device and the correspondent's computing device.

Code block 403 performs checks to determine the capabilities required for carrying out the particular handling case being considered. When code block 402 and code block 403 have completed, the then-currently available computing capabilities are compared with the capabilities required for carrying out the particular handling case being considered. Strictly as an example, if 100 MB of free memory are available and the particular handling case being considered requires only 90 MB, then that handling case is feasible at least to the extent of memory needs.

However, even if there are sufficient computer resources (e.g., CPU, memory, bandwidth) available to carry out the particular handling case being considered, that does not necessarily mean that those available resources are sufficient to implement an encryption scheme that meets any particular privacy level. Accordingly, additional determinations are made within the FORK/JOIN block.

At code block 404, a data access is made to determine a minimum privacy demand corresponding to the particular handling case being considered. Concurrently, at code block 405 within the FORK/JOIN block, a calculation is made to determine the minimum privacy achievable given the then-currently available computing capabilities.

After the JOIN, the results of code block 402, code block 403, code block 404, and code block 405 are available to test 406 as well as to test 407. The shown test 406 determines if there are sufficient CPU and memory resources available to carry out the considered handling case given the privacy demands for the considered segment record. The shown test 407 determines if there is sufficient bandwidth available to carry out the considered handling case given the privacy demands for the considered segment record. If there is not sufficient CPU and memory resources available to carry out the considered handling case given the privacy demands for the considered segment record, or if there is not sufficient bandwidth available to carry out the considered handling case given the privacy demands for the considered segment record, then that handling case is not feasible and, at step 408, that handling case is rejected so that it is not considered in the encryption type optimization operations 420.

The encryption type optimization operations 420 include steps to determine a best feasible handling case 409 and processes the segment record in accordance with that best feasible handling case. In one embodiment, if it is deemed that the considered segment record cannot be processed at that moment in time, an alternative feasible handling case is considered. Alternatively, and as shown in this embodiment, it is deemed that the considered segment record cannot be processed at that moment in time using the best feasible handling case, and thus a delay is introduced in expectation that there will be more resources available at a later time. On the other hand, if the encryption type feasibility operations 410 determine that there are no feasible handling cases, then the "No" branch of decision 411 is taken.

Otherwise, processing proceeds to step 412 to process the considered segment record based on the selected handling case. As earlier described, a particular handling case is associated with one or more encryption schemes. As such, the associated encryption scheme is applied to the segment payload, after which processing proceeds to step 414 to initiate transmission of all or portions of the encrypted payload of the segment record. Upon acknowledgement of successful receipt by the recipient, the segment is marked as complete (step 416) and the channel-driven encryption technique repeats until there are no remaining segment records to be processed.

Returning to the discussion of test 407 to determine if there is sufficient bandwidth available to carry out the considered handling case given the privacy demands for the considered segment record, it can happen that available bandwidth changes frequently, especially when the user's computing device is an edge device such as a smart phone. Accordingly, the feasibility of carrying out a particular handling case can change from "feasible" to "not feasible" at any moment in time. A transition from "feasible" to "not feasible" and back can happen independently for any handling case. Various such transitions are shown and described as pertains to FIG. 4B.

Figure 4B:
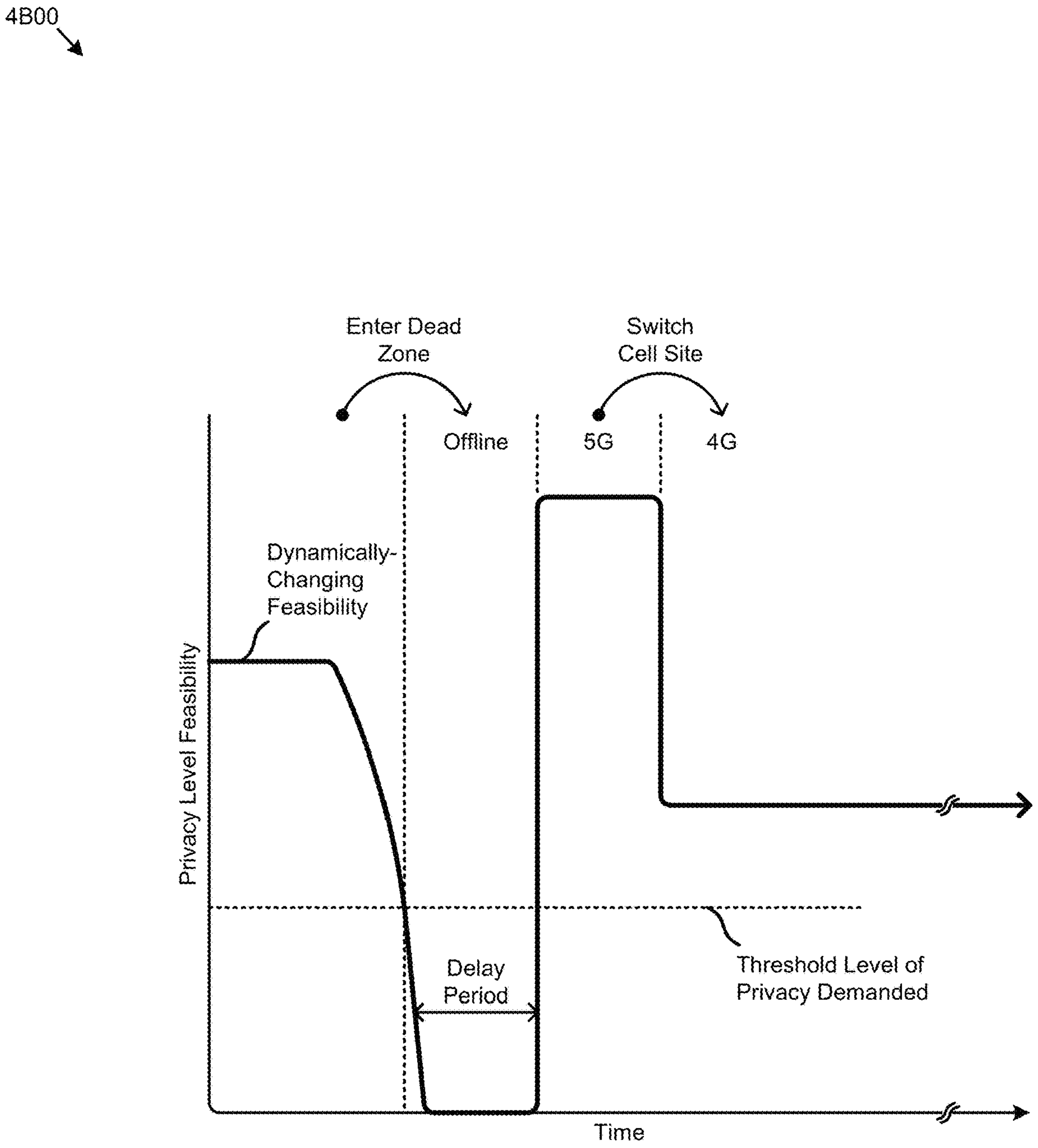
FIG. 4B is a chart showing dynamically-changing feasibility conditions as encountered when communicating between two computers involved in negotiating resource-efficient privacy-preserving transactions, according to some embodiments.

FIG. 4B is a chart showing dynamically-changing feasibility conditions 4B00 as encountered when communicating between two computers involved in negotiating resource-efficient privacy-preserving transactions.

FIG. 4B illustrates aspects pertaining to preprocessing sensitive data items to match payload content volume with end-to-end communication channel or processing capabilities. Specifically, the figure is being presented to show how the feasibility of transmitting a particular segment changes over time. More specifically, the figure depicts a dynamically-changing feasibility curve as communication channel or processing capabilities change. The figure depicts the scenario of a mobile user device moving into a dead zone (e.g., into a tunnel), then staying offline for a period, then coming out the tunnel into the proximity of a 5G cell site (i.e., high bandwidth) infrastructure, then switching into the proximity of a 4G cell site infrastructure. When determining availability of bandwidth in a communication channel, any aspect that affects bandwidth characteristics can be measured and analyzed. Strictly as examples, reading of a strong signal on a 5G channel may be used to estimate bandwidth availability and/or availability of an isochronous socket on a 4G channel can be used to estimate bandwidth availability. Furthermore, any aspect of noise (e.g., static or intermittent signal) that affects bandwidth characteristics can be used to estimate bandwidth availability, etc.

The figure also shows that during the time that one or more end-to-end Internet communication channels are unable to support handling of cases that render encryption/privacy at or above a demanded threshold level, then communication of segments is (temporarily) delayed.

Encrypted Payload Size Reduction Techniques

Returning to the discussion of FIG. 2A, specifically discussion of step 208, there are many ways to reduce the size of an encrypted payload while still preserving privacy. Several example techniques are shown and described as pertains to FIG. 5A and FIG. 5B.

Figure 5A:
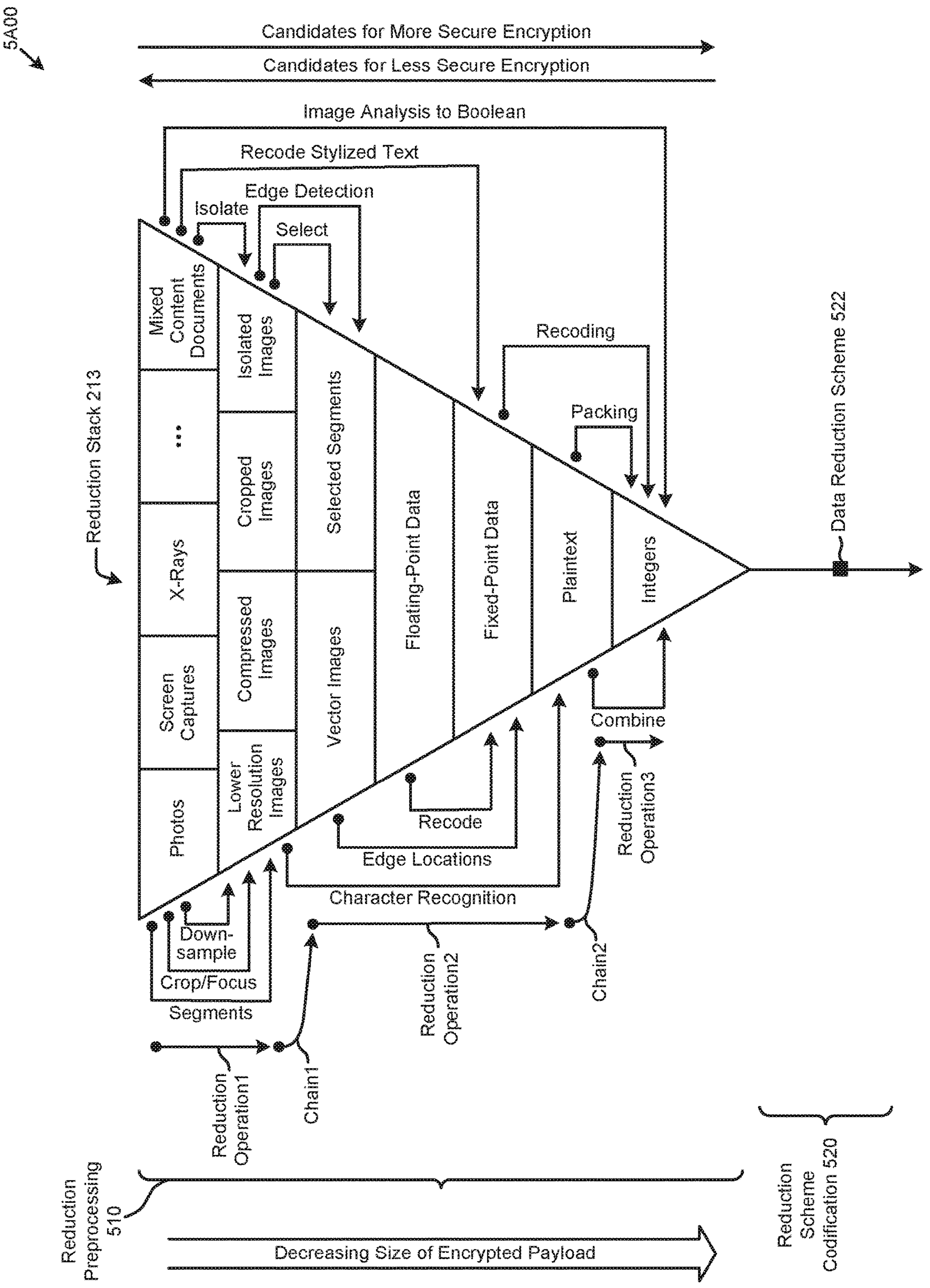
FIG. 5A is a schematic diagram showing reduction schemes as used to reduce payload size when sharing large amounts of sensitive data, according to some embodiments.

FIG. 5A is a schematic diagram showing data reduction schemes 5A00 as used to reduce payload size when sharing large amounts of sensitive data. As an option, one or more variations of data reduction schemes 5A00 or any aspect thereof may be implemented in the context of the architecture and functionality of the embodiments described herein. The data reduction schemes 5A00 or any aspect thereof may be implemented in any environment.

FIG. 5A illustrates aspects pertaining to preprocessing sensitive data items to match payload content volume with communication channel or processing capabilities. Specifically, the figure is being presented with respect to its contribution to addressing the problem of how to achieve high-performance multi-party privacy-preserving analytics even when some analytics require resource-intensive forms of homomorphic encryption.

The figure depicts a multiplicity of ways to transform from one data representation into another data representation. In doing so, the size (e.g., in bytes) of data to be processed for homomorphic encryption is reduced. Specifically, as a result of reduction of the size of the data to be processed for homomorphic encryption, less memory is demanded at the user's computing device, less CPU power is demanded at the user's computing device, less bandwidth is demanded for communication to a correspondent's device, less memory is demanded at the correspondent's device, less CPU power is demanded at the correspondent's device, and so on. Nevertheless, even though all or a portion of the original data has been reduced to fewer bytes, the actual information of interest may still have the same fidelity of meaning as before the reduction(s). Strictly as one example, consider a scenario where the answer to the question, “Am I pregnant?” or “Are you pregnant?” might be used in a correspondent’s determination of a ‘best’ healthcare plan. One way for a correspondent to make a determination or prediction of a best healthcare plan might be to combine the answer to that question against characteristics of candidate-available healthcare plans. Furthermore, one way for a correspondent to answer that question might be for the correspondent to analyze the user’s sonogram. However, the user might not want to divulge her sonogram or any information derived from her sonogram that would answer whether or not she is pregnant. Nevertheless, the answer to that question would be useful to the correspondent in making a determination of a best healthcare plan for the user.

Continuing this example, rather than send an encrypted sonogram to the correspondent in a manner that cannot be decrypted by the correspondent (i.e., since the size of which encrypted sonogram would be enormous), the user device can reduce the sonogram to one bit that represents pregnant or not pregnant, and that one bit can be sent to the correspondent in a manner that cannot be decrypted by the correspondent (but can be used in predictive analytics). In this example, a large amount of data (the sonogram image) is reduced to a small amount of data while still retaining the fidelity of certain relevant information that the large amount of data represented. Specifically, as discussed in this example, a small amount of data (e.g., a binary value for “Yes” or “No”, or ‘1’ or ‘0’) represents the answer to the question of whether or not the user is pregnant.

The foregoing is merely one example of reduction preprocessing. Many other examples are shown in the example reduction stack 213. Images can be reduced in size by being down-sampled in resolution, or by being cropped, or by being isolated (e.g., isolating one frame from a movie clip), or by being compressed, etc. In some cases, images can be reduced in size by being vectorized or by being subjected to segmentation and selection of segments of interest. In some cases, floating-point data can be reduced in size by being re-represented in rounded or otherwise reduced precision fixed-point equivalents or near equivalents. For example, the floating-point number “3.14159” can be represented as “integer portion=3” and “fractional portion=14”.

In some reduction cases, multiple data size reduction techniques of the reduction stack 213 are chained over multiple operations. For example, and as shown, a reduction operation3 (from chain2) might be performed over the results of reduction operation2 (from chain1), which in turn was performed over the results of reduction operation1. As used herein, a reduction stack is any combination of data processing techniques which, when applied to a data item of a first size, serve to reduce the size of the data item. An application of one or more of such data processing techniques to reduce the size of the data item is termed a data reduction scheme. This is depicted by reduction preprocessing step 510. Any one or more reduction stack techniques taken from the aforementioned combination of data processing techniques can be applied based on inherent or determined characteristics of the contents of the data item.

More specifically, determination of one or more data reduction schemes (e.g., which reduction operations to perform, and in which order) can be made based in part on the kind and/or sensitivity of data under consideration, and/or the determination of one or more data reduction schemes can be made based in part on the then-current conditions of the Internet channels and/or based on the then-current availability of computing resources. For example, upon having made a determination as to the kind and sensitivity of a subject portion of data, any number of candidate data reduction schemes might be evaluated (e.g., referring again to step 206 of FIG. 2A) for candidate application over the subject portion of data. Subsequently, once a particular data reduction scheme has been selected, then the data reduction scheme can be codified (e.g., by reduction scheme codification 520) into a data reduction scheme 522, and the data reduction scheme can be shared with a correspondent together with the encrypted version of reduced-size user data such that the correspondent can know the form of the encrypted data. Even though the correspondent cannot decrypt the encrypted data, the correspondent can nevertheless use the encrypted data in homomorphic computations.

The embodiment shown in FIG. 5A is merely one example. As shown, the data reduction schemes include images, floating-point data, fixed-point data, plaintext and integers, however many other data representations that have corresponding reduction operations and/or reduction paths through a plurality of reduction operations are possible. As used herein, at least in some embodiments, the term ‘reduced user data’ or ‘reduced-size user data’ refers to a given data that has been processed so as to reduce the size of the given data but while preserving at least one aspect of the meaning of the given data.

For example, consider the case where a party (e.g., an insurance underwriter) wants to know whether an applicant or an insured person cares about their financial health, physical health, and/or mental health. One way to assess this would be to analyze an image of the home screen of the applicant’s or insured person’s mobile phone. However such an image is larger than need be to answer the question. One reduction operation might be to reduce the image into a series of app names (e.g., from a known name database, or from recognition of an app’s icon). This series of app names could be further associated with the number of apps in each category of interest (e.g., financial health, physical health, or mental health). A self-care score can be calculated from such results and reduced to an integer value (e.g., a self-care score in the range from 0 to 255). As such, the data payload has been reduced from an image of many kilobytes to just one byte. Moreover, the data has been processed so as to reduce the size of the data without changing the essence of meaning of the data.

In certain embodiments, reduced user data refers to given data that has been processed so as to reduce the size of the given data while changing the meaning of the given data only by a calculable amount. For example, a floating-point value “3.14159” can be represented as “integer portion=3” or “fractional portion=14” while changing the precision of the value only by 159 thousandths. In certain embodiments, reduced user data refers to given data that has been processed so as to reduce the size of the given data while changing the resolution of the given data only by a calculable amount. For example, a 32-bit color depth image can be represented as a 16-bit color depth image, changing the image color depth to be represented in only two bytes per pixel rather than four bytes. The foregoing discussion of FIG. 5A includes some techniques for codifying a reduction path or operation into a designation that can be shared with a correspondent.

Many practical scenarios emerge. As one example, and as heretofore described, homomorphic encryption allows computation on encrypted data such as an encrypted payload. However, in secure multi-party computation settings, the parties need to agree on the form and/or format of the corresponding encrypted payload. More particularly, the parties need to agree on the form and/or format of the corresponding encrypted payload to the extent that the form and format of the operands and the form and format of the operator is agreed-to prior to commencement of the secure computation.

Encryption of Payloads to Support Arbitrarily-Complex Computations

Some early homomorphic encryption techniques only supported additions of two numbers, such as in A+B=SUM. Specifically, the encrypted values enc(A)+enc(B) can be added together form enc (SUM). The operands as well as the result are always encrypted such that no decryption key is needed by the entity that performs the computations. The result of the computation, specifically enc (SUM), if decrypted, would be the same SUM as would be computed using unencrypted values A and B. Further development of homomorphic encryption allowed for multiplication of encrypted values into an encrypted product such that enc (A)*enc(B) can be multiplied together to form enc (PRODUCT).

As previously described, cryptosystems exist that support arbitrary computation on ciphertexts. As such, any arbitrary sequence of operations (e.g., a program) can be performed over encrypted operands to form an encrypted result. That is, the cryptosystem can be configured such that enc (RESULT)=F(enc(A), enc(B)), where F is the arbitrary sequence of operations performed over enc(A) and enc(B). In such a cryptosystem, the entity that performs the arbitrary sequence of operations over enc(A) and enc(B) need never hold a decryption key to decrypt enc(A) and/or enc(B) and/or need never hold a decryption key to decrypt enc (RESULT) and, as such, the unencrypted nature of both the operands and the result are never known to the entity that performs the arbitrary sequence of operations.

A cryptosystem that is so configured can be used wherever sensitive information is exchanged between parties and/or where privacy is to be maintained, even though sensitive information is exchanged with an untrusted third party. For an untrusted third party to be able to perform an arbitrary sequence of operations over arbitrary inputs, the untrusted third party needs to know what arbitrary sequence of operations is to be performed (e.g., a name or identifier of a program) and, furthermore, the untrusted third party needs to know enough about the form and format of the inputs such that the program can use the given inputs as needed (e.g., as needed by the program) so as to return the sought-after computation result. For example, it can happen that the computation of function F(enc(A), enc(B)) is different from the computation of F(enc(B), enc(A)). Moreover, in some cases (e.g., where the arguments of the function F are not commutative), the computation of F(enc(B), enc(A)) would return a wrong result. Accordingly, the untrusted third party would need to receive an instruction to perform computation of function F using enc(A) as the first operand of F, and using enc(B) as the second operand of F.

Unfortunately, it is unscalable to force all of the aforementioned blind third parties to keep up to date with all possible sequences of operations over all possible operand encryption variations that could arise from the application of one or more techniques for data size reduction. Rather, some means needs to be in place to be able to let the blind third party know the specific representation of a shared operand, even though the shared operand had been subjected to one or more data size reduction operations.

To emphasize the criticality of the parties agreeing on the form and format of an operand, consider a variation of function F, call it F1, where the form of F1's operands are different from the form of operands of F. The sequence of operations of F1 can be such that the encrypted result of F1 (enc(A1), enc(B1)) is equal to the encrypted result of F(enc(A), enc(B)). In this case, the untrusted third party would need know to perform computation F1 by using enc (A1) to interpret the first operand of F1, and by using enc(B1) to interpret the second operand of F1.

This situation becomes more complicated when the form of the operands may vary, for example based on some pre-processing performed over an operand before being encrypted and sent to the untrusted third party. Consider pre-processing of an operand A (e.g., an image) to form operand A1 which is a list of shapes (e.g., {rectangle, circle, ellipse}) codified in accordance with an operand of "type O1" that can be sent to a untrusted third party. The untrusted third party would need to know that enc (A1) is indeed formatted as an operand in accordance with "type O1" and, as such, the untrusted third party would use enc (A1) for any operations F, F1, . . . Fn and/or any other functions that expect an operand of "type O1".

This situation becomes even more complicated by the fact that, when using FHE, operands are frequently reduced in size using combinations and/or sequences of data size reduction techniques so as to facilitate communication of operands over the Internet to the untrusted third party. Since there are many data size reduction techniques, and since any combination or sequence of such data size reduction techniques can be chained, this situation leads to an explosion in possible operand types and/or possible chains or sequences of data size reduction techniques. Some means needs to be in place such that the parties can agree on the form and format of the shared encrypted data, even though the shared encrypted data had been subjected to one or more forms of data size reduction.

This need for the parties to agree on the form and format of the shared encrypted data becomes even more critical when the form and format of the shared encrypted data is determined based on the then-current conditions of the Internet channels between the parties, and/or based on the then-current availability of computing resources available for computation and/or constraints (e.g., degree of privacy) as may be demanded by one or another party with access to the shared encrypted data.

To illustrate, it can happen that one particular encryption technique and/or one particular data reduction technique might be used at a first moment in time (based on the then-current conditions of the Internet channel at that moment), whereas a different particular encryption technique and/or one particular data reduction technique might be used at a second moment in time (based on the then-current conditions of the Internet channel at that second moment). It can also happen that one particular encryption technique and/or one particular data reduction technique might be used when both parties have highly-capable computing resources available for computation (e.g., powerful servers), whereas a different encryption technique and/or data reduction technique might be used when one party has only a less-capable computing platform (e.g., a smart phone) available for computation at a particular moment in time.

As such, some means needs to be in place such that the particular encryption technique to be used, as well as any particular data reduction technique (e.g., combination or sequence of reduction techniques), can be negotiated at a particular moment in time just prior to carrying out the data size reduction techniques and just prior to transmitting the shared encrypted data. Moreover, some means needs to be in place such that it is possible to optimize the result of the negotiation based on an optimization priority that is used (e.g., in an optimization function) as merely one of several optimization variables. One such technique for negotiating point-in-time payload reduction is shown and described as pertains to FIG. 5B.

FIG. 5B depicts a routine 5B00 used in negotiating point-in-time payload reduction schemes when two computers are involved. As an option, one or more variations of routine 5B00 or any aspect thereof may be implemented in the context of the architecture and functionality of the embodiments described herein. The routine 5B00 or any aspect thereof may be implemented in any environment.

As used herein a payload reduction scheme includes specification of one or more data size reduction techniques, as well as specification of one or more encryption techniques. In some cases, aspects of a payload reduction scheme may be based on negotiations over, and agreement on, a particular privacy index, which in turn may imply a particular security level. In some cases, aspects of a payload reduction scheme may be based on negotiations over, and agreement on, a particular security level. To illustrate, the size of the payload of a segment record (e.g., encrypted payload 334, clear text payload 332) can vary greatly based on a determination of which encryption algorithm and which settings should be used when producing an encrypted payload of a segment record. Strictly as examples, a payload that is protected by SMC will typically be significantly smaller than the same payload protected by lattice cryptography. Moreover, the same payload protected by different choices of the security parameter n and the modulus q can cause the payload to vary dramatically in size.

Routine 5B00 of FIG. 5B is shown as an implementation of step 208. The specific steps shown include step 550 to negotiate data size reduction techniques that, once applied, serve to reduce the size of shared data prior to encryption, step 552 to codify a data reduction scheme based at least in part on the negotiated one or more data size reduction techniques, and step 554 to store the codified data reduction scheme into a payload of segment record (e.g., into a data reduction scheme field 337 shown in FIG. 3B). At step 556, the one or more data size reduction techniques are actually applied prior to the time when the reduced size data is shared with a correspondent. The contents of the data reduction scheme field itself can be unencrypted (as depicted in FIG. 3B), or the contents of the data reduction scheme field can be encrypted using a symmetric encryption algorithm or an asymmetric encryption algorithm, or any other known-in-the-art encryption algorithm.

One result of the negotiation of step 550 is a negotiated data reduction scheme, which can be codified into a negotiated data reduction scheme object 523. For example, a negotiated data reduction scheme might be "first crop, then apply character recognition," and that description might be codified (step 552) into a string or other object containing "{Crop, OCR}". Further, that string or another object might be stored (step 554) into a bitfield of a segment record. The negotiated data size reduction techniques can be applied to corresponding data items (step 556) to generate reduced-size data, which reduced-size data can be encrypted and then transmitted over the Internet (e.g., as a segment record) to a correspondent.

When the correspondent receives the reduction path description (e.g., as may be codified into a data reduction scheme field 337), the correspondent can then know the form and/or format of the corresponding encrypted payload. In some cases, each correspondent can know the form and/or format of the corresponding encrypted payload based on an a priori agreement. In other cases, the form and/or format of any particular encrypted payload can be negotiated by the parties prior to data reduction. Moreover, the negotiated form and/or format of any particular size-reduced payload can be negotiated at any point in time based on the then-current, dynamically-changing conditions.

When data reduction operations are performed based on dynamically-changing conditions, the parties involved in sharing the data need to reach a point-in-time understanding of how the data has been reduced. One possible technique for dynamic, point-in-time negotiation of one or more data size reduction techniques to apply to the data is given in FIG. 5C.

Figure 5C:
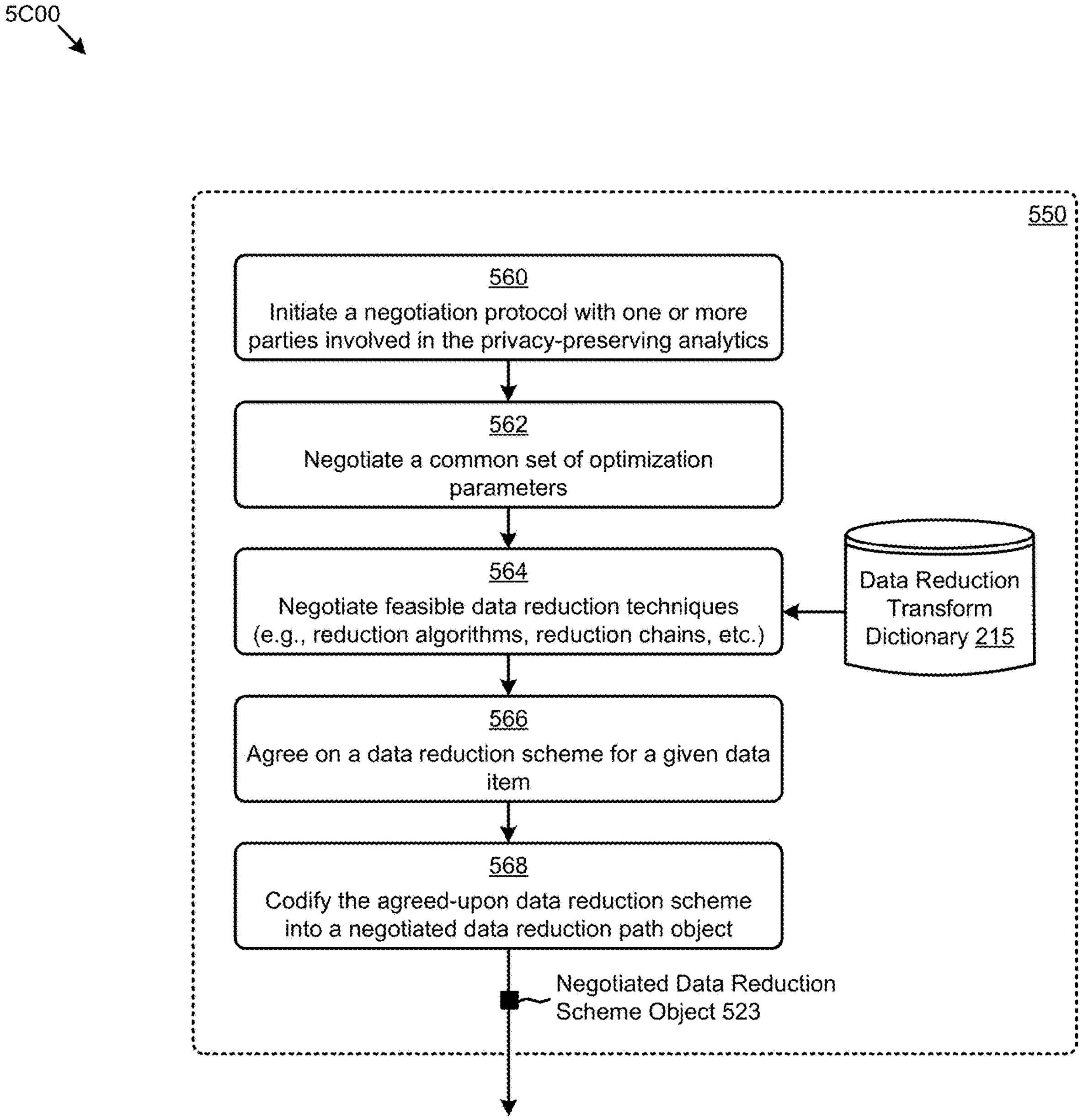
FIG. 5C depicts a routine used in negotiating point-in-time payload reduction schemes when two computers are involved, according to some embodiments.

FIG. 5C depicts a routine 5C00 used in negotiating point-in-time payload reduction schemes when two computers are involved, according to some embodiments. As an option, one or more variations of routine 5C00 or any aspect thereof may be implemented in the context of the architecture and functionality of the embodiments described herein. routine 5C00 or any aspect thereof may be implemented in any environment.

The embodiment shown in FIG. 5C is merely for illustration. Other techniques for negotiation of one or more data size reduction techniques are possible. The particular routine 5C00 commences by a first party initiating a protocol with another party that is involved in privacy-preserving analytics (step 560). The protocol is carried out so as to (1) negotiate a common set of optimization parameters (step 562), (2) negotiate feasible data reduction techniques (step 564), and (3) agree on a particular feasible data reduction scheme for each given data item (step 566).

When negotiating a common set of optimization parameters (step 562) the parties may agree on a particular privacy level. Such a privacy level can be quantified as a privacy index, where a greater value connotes more privacy as compared to a privacy index of a lesser value. In some cases a first party may enforce a greater privacy index than a second party. In such cases, and to the extent possible, the second party will agree to observe the greater privacy level. In some cases, a particular privacy level offered by a first party cannot be agreed-to by the second party. In such cases, the parties may negotiate to agree to change the privacy level to a lesser value. In other situations, when a particular privacy level offered by a first party cannot be agreed to by a second party, and a lower privacy level is not available (e.g., due to any one or more constraints on the privacy level, or due to any other feasibility conditions), the parties may negotiate to delay further correspondence until a later point in time.

When negotiating feasible data reduction techniques (step 564), data reduction transform dictionary 215 may be consulted. Such a data reduction transform dictionary may refer to any/all aspects of reduction stack 213. In particular, a data reduction transform dictionary may include entries for data reduction operations (e.g., crop, downsample, recode, etc.), as well as chains (e.g., chain1, chain2, etc.). The entries of such a data reduction transform dictionary may further include an indication of the extent to which a particular operation or chain will reduce a particular type of input data. Still further, the entries may further include an indication of whether a particular data reduction operation or chain is a candidate for a more (or less) secure encryption.

After considering at least some of the feasible data reduction techniques and, more specifically, after considering at least some of the feasible data reduction techniques that in combination satisfy the negotiated optimization parameters, step 566 serves for the parties to reach agreement on a particular feasible data reduction scheme for a given data item. The negotiated agreement as to what data reduction techniques are to be used for a given data item can then be codified (step 568) into a negotiated data reduction scheme object 523. Such a negotiated data reduction scheme object 523 can be provided to the caller of routine 5C00. Routine 5C00 can be repeated any number of times so as to negotiate between the parties for any number of data items.

In other situations, when negotiating a common set of optimization parameters (step 562) and/or when negotiating feasible data reduction techniques (step 564), the parties may agree on the then-current conditions of the Internet channels and/or may agree on the then-current availability of computing resources.

Referring again to step 564 of FIG. 5C, a data reduction transform dictionary 215 may be consulted. One possible embodiment of a data reduction transform dictionary is shown and described as pertains to FIG. 5D.

Figure 5D:
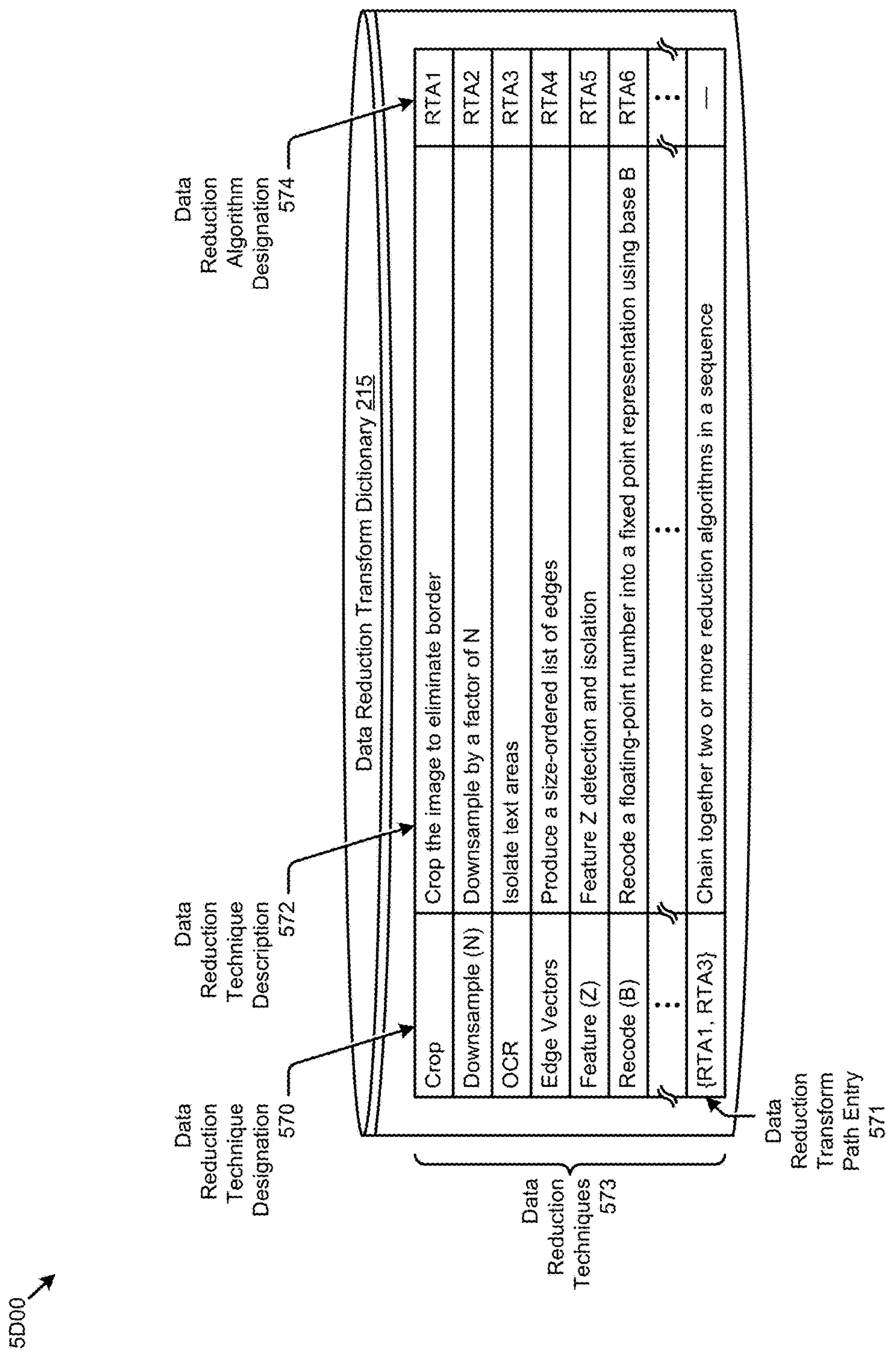
FIG. 5D depicts an illustrative data reduction transform dictionary implementation as used in negotiating point-in-time payload reduction schemes, according to some embodiments.

FIG. 5D depicts an illustrative data reduction transform dictionary implementation 5D00 as used in negotiating point-in-time payload reduction schemes, according to some embodiments. As an option, one or more variations of data reduction transform dictionary implementation 5D00 or any aspect thereof may be implemented in the context of the architecture and functionality of the embodiments described herein. The data reduction transform dictionary implementation 5D00 or any aspect thereof may be implemented in any environment.

As earlier indicated, various parties may agree on the form and/or format of any data item based on an a priori agreement, or, the form and/or format of any particular data item can be negotiated by the parties prior to data reduction over the particular data item. One scenario for various parties to reach a negotiated agreement involves consulting a data reduction transform dictionary 215. Specifically, the parties may agree at first to use some particular data reduction transform dictionary, and thereafter, the parties can carry out a protocol that reaches agreement between the parties as to what specific data reduction scheme is optimal, given (1) the combination of any optimization priorities and/or other constraints as may be imposed by one or the other party to the negotiation, and (2) characteristics pertaining to the then-current conditions. Continuing the foregoing scenario, since the parties had earlier agreed to use some particular data reduction transform dictionary, when a particular data reduction technique or series of data reduction techniques is to be considered during the course of the negotiation, it can be referred to unambiguously by an entry-specific data reduction technique designation 570 (e.g., "Crop", as shown) and/or by an entry-specific data reduction algorithm designation 574 (e.g., RTA1, RTA2, as shown).

As used herein a data reduction transform dictionary is any representation of one or more data reduction transform algorithms (e.g., by a numeric value, or by a string value, etc.). A data reduction transform dictionary can be shared in any public Internet location without loss of privacy of the data to be operated on by the or one or more data reduction transform algorithms that correspond to entries in the data reduction transform dictionary. In some cases, such as is shown in the specific reduction transform dictionary implementation 5D00, a data reduction transform dictionary entry may include any number of data reduction techniques 573, individual ones of which correspond to a data reduction technique description 572. While such a description may aid in human cognition, computer-to-computer protocols can rely on computer-readable values given by data reduction technique designation 570 and/or by data reduction algorithm designation 574, or combinations thereof.

In some cases, such as is shown in the specific data reduction transform dictionary implementation 5D00, a data reduction transform dictionary entry may include a data reduction transform path entry 571, which entry designates a sequence of two or more instances of reduction technique algorithm designations. Strictly as an example, and as shown, a sequences of two or more instances of reduction technique algorithm designations can be codified into strings or other objects that can be communicated in Internet messages. In the example shown, the data reduction transform path entry 571 in the bottom entry of the data reduction transform dictionary refers to a reduction path formed by applying a "Crop" algorithm (e.g., RTA1) followed by an OCR algorithm (e.g., RTA3). This path is codified in the string "{RTA1, RTA3}".

Additionally or alternatively, rather than reaching an agreement to use some particular data reduction transform dictionary and entries therefrom, upon negotiation of other terms of a transaction, a sending correspondent (e.g., a source device) might send actual computer-readable code that implements the data reduction transform to a recipient (e.g., a worker device). In such cases, the sending correspondent and the recipient might negotiate the particular form of the code that performs a particular data reduction algorithm. For example, a particular form of the data reduction algorithm code to be sent might be negotiated to be sent as platform-specific binary code, or might be negotiated to be sent as a platform-independent script. In some cases, the two parties might agree to use a third party (e.g., an algorithm-as-a-service provider) to perform some or all of the particular data reduction algorithm.

One technique to enable participants to reach agreement as to the terms of any particular resource-efficient privacy-preserving transaction involves a computer-to-computer protocol.

Figure 6B:
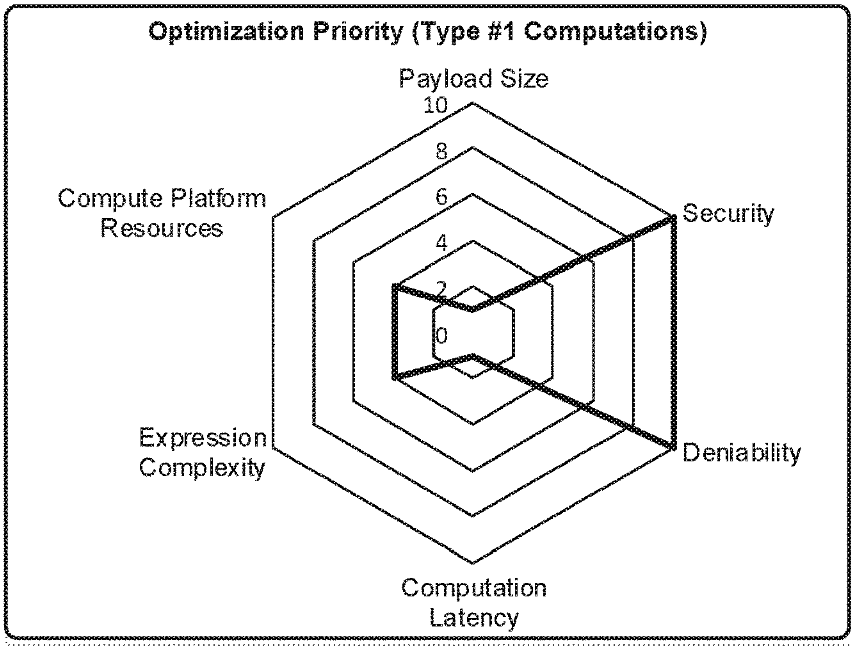
FIG. 6B, FIG. 6C, and FIG. 6D depict different example optimization priorities, according to some embodiments.
Figure 6C:
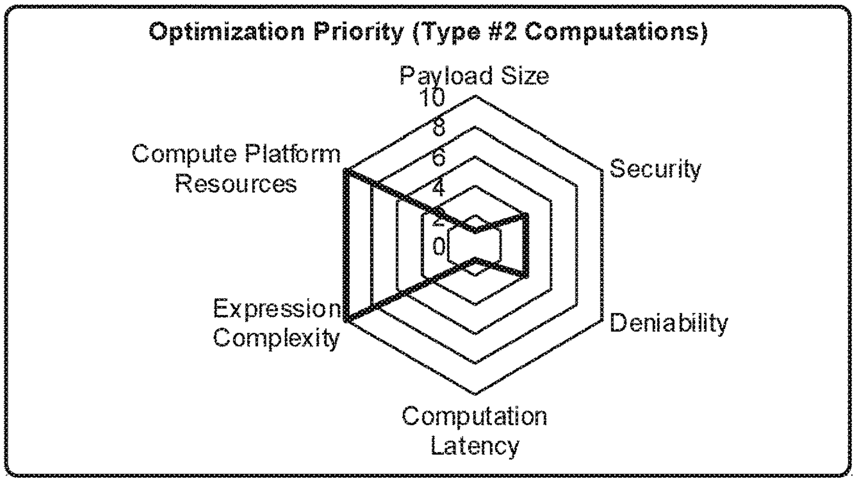
Figure 6D:
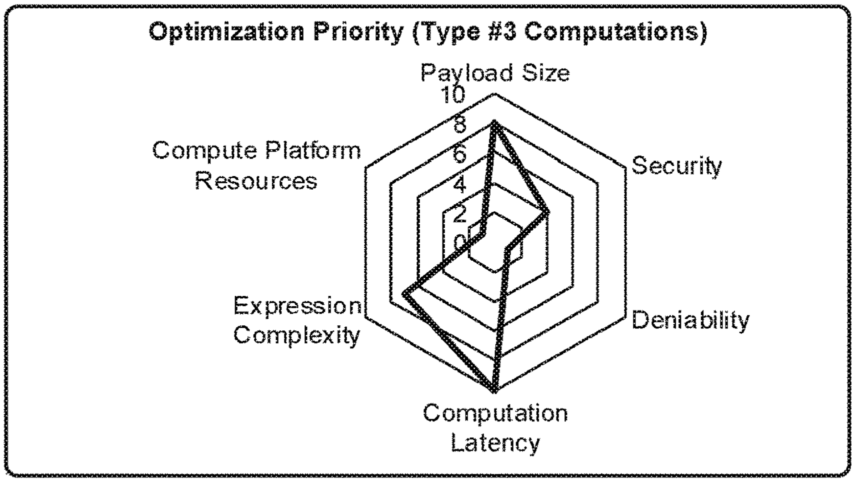
Figure 6A:
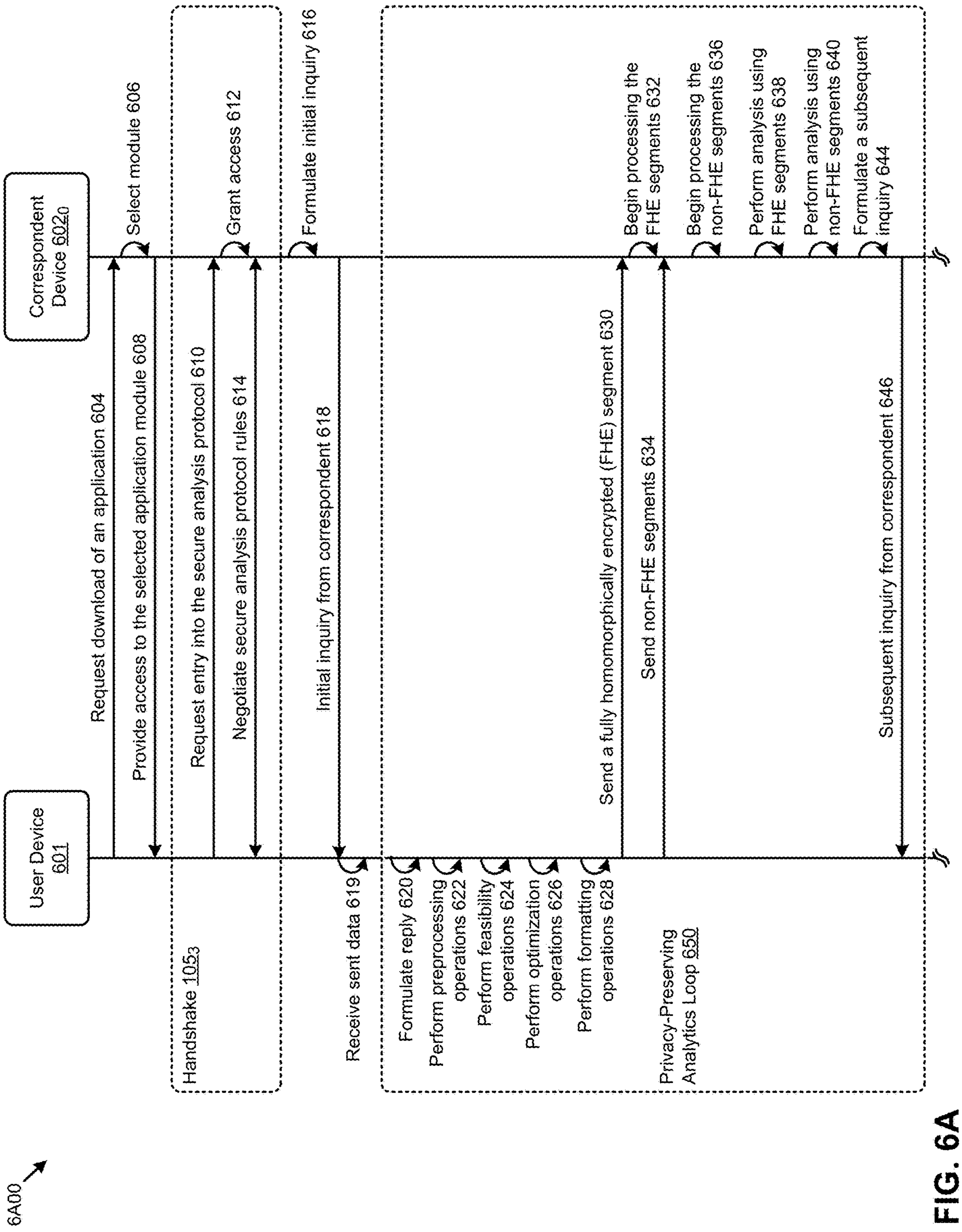
FIG. 6A is a protocol diagram showing how participants carry out payload reduction schemes when two computers are involved in negotiating resource-efficient privacy-preserving transactions, according to some embodiments.

FIG. 6A is a protocol diagram 6A00 showing how participants carry out payload reduction schemes when two computers are involved in negotiating resource-efficient privacy-preserving transactions. As an option, one or more variations of protocol diagram 6A00 or any aspect thereof may be implemented in the context of the architecture and functionality of the embodiments described herein. The protocol diagram 6A00 or any aspect thereof may be implemented in any environment.

FIG. 6A illustrates aspects pertaining to preprocessing sensitive data items to match payload content volume with communication channel or processing capabilities. Specifically, the figure is being presented with respect to the disclosed machine-to-machine protocol for achieving high-performance, multi-party privacy-preserving analytics even when some analytics require homomorphic encryption.

As shown, the protocol is carried out between a user device 601 and a correspondent device $\mathbf{602_0}$ to implement a method for performing negotiated resource-efficient privacy-preserving transactions. The shown protocol commences when correspondent device $\mathbf{602_0}$ receives a request (e.g., message 604) from user device 601 to download a module (e.g., a sequence of instructions) of an application.

A computing agent at the correspondence device then selects an applicable module (operation 606) and responds to the request by providing access to the selected application module (message 608). The access may be in the form of a download to the user device, or the access may be in the form of a URL to an Internet resource (e.g., a webservice or web app component, etc.). Upon providing access to a sequence of instructions comprising the module, the user device commences to execute a sequence of instructions that are configured to negotiate ongoing communications (e.g., perform a handshake $\mathbf{105_2}$) and thereafter enter into a privacy-preserving analytics loop 650, where some but not all exchanges of data within Internet packets are encrypted using fully homomorphic encryption.

The aforementioned handshake serves to establish an Internet communication channel between the user device and a correspondent device and, in some cases, the two devices agree on which communication protocols and/or encryption algorithms are candidates to be used in the ongoing Internet communications. Once at least one protocol and/or encryption algorithm has been agreed upon by the two devices, then the devices can carry out further communications. In some cases, and as shown, aspects of the negotiation and determination of underlying encryption protocols are themselves proprietary between the two devices and, as such, the user device will request entry (e.g., via message 610) into a secure analysis protocol. Assuming the correspondent device honors the request, then the correspondent device grants access (operation 612) and the user device can continue (e.g., via bidirectional exchange 614) to negotiate use of further secure analysis, including secure analysis protocols, and secure analysis rules.

The correspondent device formulates an initial inquiry 616, which is packaged into data that is in turn sent to the user device (message 618). In the shown portion of the protocol, the user device receives at least a portion of the sent data from the correspondent device (operation 619).

The user device enters into a privacy-preserving analytics loop 650 and, using at least some of the sequence of instructions, formulates a reply (operation 620) to the initial inquiry 616, using at least a portion of the data sent from the correspondent device. Formulating a reply may include calculating a multi-segment response to the sent data. Specifically, and as shown, formulating a reply includes performance of preprocessing operations (operation 622), performance of feasibility operations (operation 624), performance of optimization operations (operation 626), and performance of formatting operations (operation 628).

In exemplary embodiments, the preprocessing operations operate over data at the user device to form a first set of user data and a second set of user data, the first set of user data comprising reduced user data. The reduced user data is subjected to encryption using a fully homomorphic encryption algorithm, which is then segmented into multiple Internet packets, where encrypted versions of the reduced user data are used to form one or more segments of a multi-segment response to the inquiry. In such exemplary embodiments, only the reduced user data is subjected to encryption using a fully homomorphic encryption algorithm, whereas other data that is not the reduced user data is encrypted using an encryption algorithm other than the fully homomorphic encryption algorithm.

In this particular scenario, any number of fully homomorphically encrypted FHE segments (message 630) are transmitted over the Internet communication channel to the correspondent device $\mathbf{602_0}$, followed by any number of non-fully homomorphically encrypted segments (message 634). Upon receipt of any segment, the correspondent device can choose to begin processing the FHE segments 632 or the correspondent device can choose to begin processing the non-FHE segments 636. When a sufficient number of segments have been received by the correspondent device, the correspondent device can perform analysis on FHE segments (operation 638). Similarly, when a sufficient number of segments have been received by the correspondent device, the correspondent device can perform analysis on non-FHE segments (operation 640).

Based on operation results stemming from the analysis on FHE segments and/or the analysis on non-FHE segments, the correspondent device can formulate a subsequent inquiry (operation 644). The subsequent inquiry (message 646) and any additional data is sent to the user device, and the privacy-preserving analytics loop 650 enters a next iteration.

The foregoing discussion of FIG. 6A discloses a protocol that applies to any sort of data that is deemed by a user to be secret, proprietary, or otherwise sensitive data. Such secret, proprietary, or otherwise sensitive data may be found in any form, and/or may pertain to data as found in any one or more of a variety of practical applications. In exemplary cases, sensitive data may be handled differently based on combinations of priorities, constraints, and any of a variety of then-current conditions. Moreover, specific techniques for handling sensitive data can be optimized based on a quantitative optimization function. Such an optimization function can be defined for any optimization priority.

As used herein, an optimization function is a mathematical expression that interrelates several factors such that a greater value is output when the output nears an optimal value. Evaluation of an optimization function may be subject to one or more constraints. If all of the one or more constraints are satisfied, the evaluation of the optimization function results in a feasible solution. Optimization functions such as the foregoing can be used to determine feasible payload reduction schemes. In some situations, optimization functions such as the foregoing can be used to determine one or more optimal payload reduction schemes.

A protocol that seeks a common optimization approach can be carried out between the parties such that the then-current set of conditions are considered for determination of an optimal payload reduction scheme while observing a given optimization priority. Example optimization priorities are shown and described as pertains to FIG. 6B, FIG. 6C, and FIG. 6D.

FIG. 6B, FIG. 6C, and FIG. 6D depict different example optimization priorities.

Specifically, graph 6B00 shows one optimization priority where security and deniability are assigned numerically greater values as compared to payload size, availability of compute platform resources, expression complexity, and computation latency. Graph 6C00 shows an alternative optimization priority where availability of compute platform resources and expression complexity security are assigned numerically greater values as compared to payload size, security, deniability and computation latency. Graph 6D00 shows yet another alternative optimization priority where payload size and computational latency are assigned numerically greater values as compared to availability of compute platform resources, expression complexity, security, and deniability.

Any of the foregoing optimization priorities can be tied to a commercial transaction. For example, different types of insights that could be extracted from the analytics might command respectively different commercial values (e.g., pricing for a transaction, pricing of a subscription, etc.).

Similarly, different extents of expression complexity might command respectively different commercial values. In some situations, an offered price, or an offered subscription level might be cast as an input into an exchange or auction. In such cases, one correspondent (e.g., a first source device) might offer a first dollar amount (e.g., an offered amount) for results of performance of an operation of a particular complexity, whereas a second correspondent (e.g., a second source device) might offer a second dollar amount (e.g., a higher offered amount) for results of performance of the same operation of the same complexity. As such, it might be that the second correspondent wins the auction. The offered amount might be included as an optimization priority and/or as an optimization variable or constraint in an optimization function.

Of course, many optimization priorities can be included in an optimization function. Numeric values can be defined for any optimization priority such that, for example, more important optimization priorities are associated with a greater numeric value as compared with less important optimization priorities. Moreover, protocols that seek a common optimization approach can be carried out between the parties such that the then-current set of conditions are considered for determination of an optimal payload reduction scheme while still observing a given set of optimization priorities. Such protocols are shown and described as pertains to FIG. 6E and FIG. 6F.

Figure 6E:
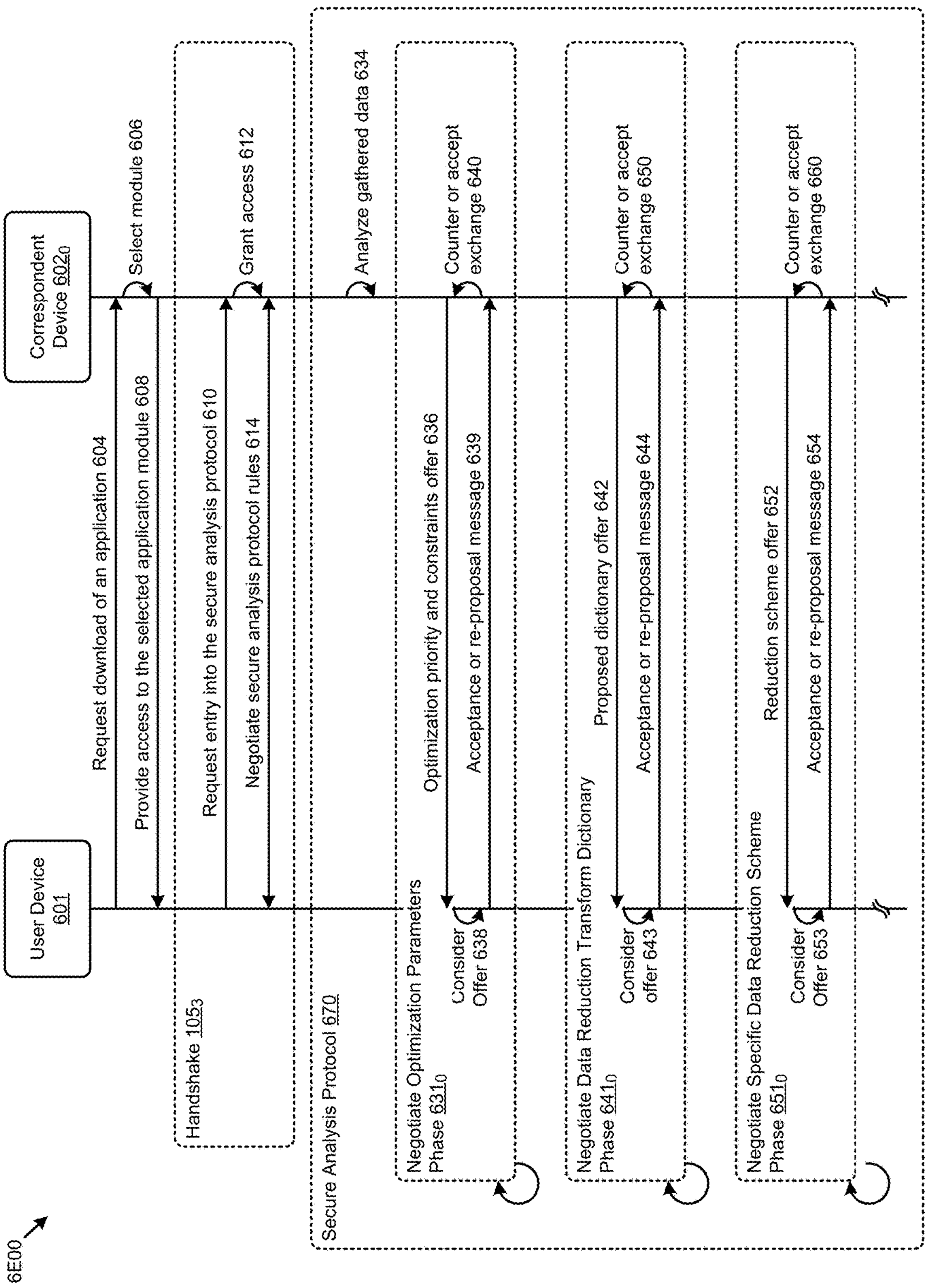
FIG. 6E is a protocol diagram showing how participants negotiate payload reduction schemes when two computers are involved in negotiating point-in-time resource-efficient privacy-preserving transactions, according to some embodiments.

FIG. 6E is a protocol diagram 6E00 showing how participants negotiate payload reduction schemes when two computers are involved in negotiating point-in-time resource-efficient privacy-preserving transactions, according to some embodiments. In the example shown, a negotiation protocol is carried out between a user device 601 and a correspondent device $\mathbf{602}_0$ to implement a method for performing negotiated resource-efficient privacy-preserving transactions. The shown protocol commences when correspondent device $\mathbf{602}_0$ receives a request (e.g., message 604) from user device 601 to download a module (e.g., a sequence of instructions) of an application. A computing agent at the correspondent device $\mathbf{602}_0$ then selects an applicable module (operation 606) and responds to the request by providing access to the selected application module (message 608). Upon providing access to a sequence of instructions comprising the module, the user device commences to execute a sequence of instructions that are configured to negotiate ongoing communications (e.g., perform a handshake $\mathbf{105}_3$) and thereafter enter into further negotiations.

In the example shown, user device 601 requests entry (message 630) into the secure analysis protocol 670. Once a set of secure analysis protocol rules has been agreed upon by the two devices (e.g., via bidirectional exchange 614), then the correspondent device grants access (operation 612). The correspondent device and the user device can bi-directionally continue to further negotiate how secure analysis is to be carried out. More specifically, the correspondent device and the user device can negotiate (1) optimization parameters, (2) determination of and use of a shared data reduction transform dictionary, and (3) any one or more specific data reduction schemes.

As shown, the user device 601 and the correspondent device $\mathbf{602}_0$ enter into a first phase (e.g., phase $\mathbf{631}_0$) of an overall negotiation whereby one party in the negotiation (e.g., correspondent device $\mathbf{602}_0$) makes an offer (message 636) comprising a set of optimization parameters (e.g., optimization priorities and optimization constraints). The other party considers the offer (operation 638) and either accepts the offer (operation 640) or re-proposes another offer (message 639). The process of making an offer, consideration of the offer, possible acceptance or re-proposal, consideration of a re-proposal, and issuance of a counter-offer or acceptance continues between the parties until the parties agree. In the shown example, once the parties agree on the optimization parameters (e.g., in phase $\mathbf{631}_0$), the negotiation moves to a next phase in the overall negotiation.

In the next phase (phase $\mathbf{641}_0$) of the overall negotiation, the user device 601 and the correspondent device $\mathbf{602}_0$ enter into a negotiation whereby one party in the negotiation (e.g., correspondent device $\mathbf{602}_0$) makes an offer (message 642) referring to a particular dictionary (e.g., a proposed data reduction transform dictionary offer). The other party considers the offer (operation 643) and either accepts the offer (operation 650) or re-proposes another offer (message 644). The process of making an offer, consideration of the offer, possible acceptance or re-proposal, consideration of a re-proposal, and issuance of a counter-offer or acceptance continues between the parties until the parties agree. In the shown example, once the parties agree on the dictionary to be used (e.g., in phase $\mathbf{641}_0$), the negotiation moves to next steps in the overall negotiation.

In the next phase (phase $\mathbf{651}_0$) of the overall negotiation, the user device 601 and the correspondent device $\mathbf{602}_0$ enter into a negotiation whereby one party in the negotiation (e.g., correspondent device $\mathbf{602}_0$) makes a reduction path offer (message 652) referring to a particular data reduction scheme (e.g., as drawn from the agreed-upon data reduction transform dictionary). The other party considers the offer (operation 653) and either accepts the offer (operation 660) or re-proposes another offer (message 654). The process of making an offer, consideration of the offer, possible acceptance or re-proposal, consideration of a re-proposal, and issuance of a counter-offer or acceptance continues between the parties until the parties agree. In the shown example, once the parties agree on a particular data reduction scheme (e.g., in phase $\mathbf{651}_0$) for a particular data item, then this phase of the overall negotiation is deemed to be complete.

In some situations, there may be more than two parties involved in the negotiation. In such cases, negotiations can be carried out under a cascaded regime, where a first negotiation is carried out by a first pair of participants, after which as second negotiation is carried out by a second pair of participants. This is shown and described as pertains to FIG. 6F.

Figure 6F:
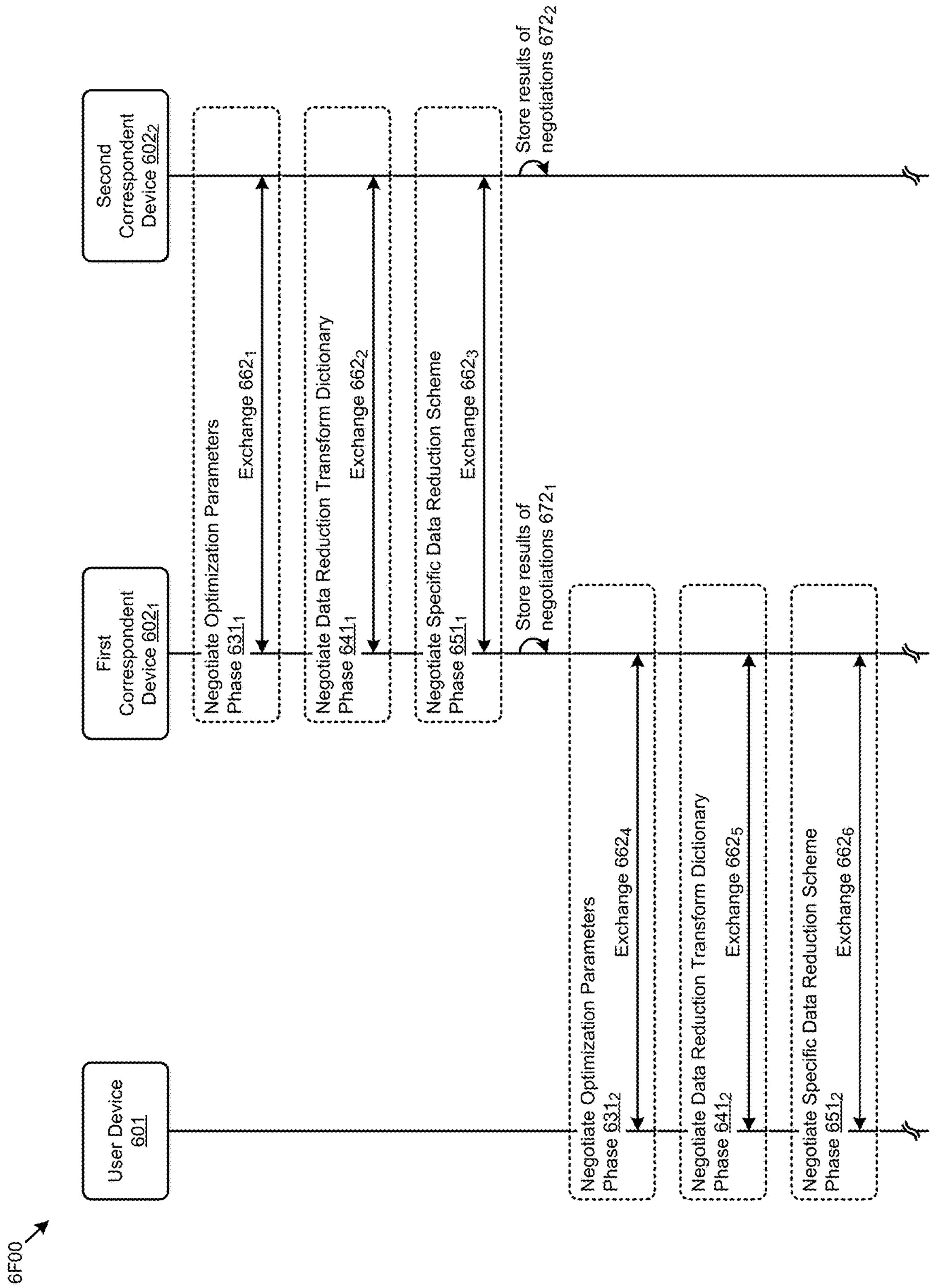
FIG. 6F is a protocol diagram showing how participants negotiate payload reduction schemes when three or more computers are involved in negotiating point-in-time resource-efficient privacy-preserving transactions, according to some embodiments.

FIG. 6F is a protocol diagram 6F00 showing how participants negotiate payload reduction schemes when three or more computers are involved in negotiating point-in-time resource-efficient privacy-preserving transactions.

In this example protocol, a first correspondent device $\mathbf{602}_1$ negotiates with a second correspondent device $\mathbf{602}_2$. As shown, the negotiation between the first correspondent device $\mathbf{602}_1$ and the second correspondent device $\mathbf{602}_2$.covers negotiation of optimization parameters (phase $\mathbf{631}_1$ and exchange $\mathbf{662}_1$), negotiation of a data reduction transform dictionary (phase $\mathbf{641}_1$ and exchange $\mathbf{662}_2$), and negotiation of a specific data reduction scheme (phase $\mathbf{651}_1$ and exchange $\mathbf{662}_3$). When the first correspondent device $\mathbf{602}_1$ and the second correspondent device $\mathbf{602}_2$ have reached agreement, the correspondents each store (via operation $\mathbf{672}_1$ and operation $\mathbf{672}_2$) results of the negotiations. The stored results of the negotiations can be used in further negotiations with further participants. Specifically, and as shown, first correspondent device $\mathbf{602}_1$ carries out a negotiation with user device 601. During the time when the first correspondent device $\mathbf{602}_1$ is involved in negotiation with user device 601, the first correspondent device $\mathbf{602}_1$ can refer to previously negotiated and saved terms. Specifically, the previously negotiated and saved terms are used during negotiation of optimization parameters (phase $\mathbf{631}_2$ and exchange $\mathbf{662}_4$), negotiation of a data reduction transform dictionary (phase $\mathbf{641}_2$ and exchange $\mathbf{662}_5$), and negotiation of a specific data reduction scheme (phase $\mathbf{651}_2$ and exchange $\mathbf{662}_6$). As such, any agreements as to constraints, and/or any agreements to use a particular dictionary, and/or any agreements as to aspects of a negotiated data reduction scheme can be cascaded from one pair of participants to another pair of participants where at least one participant is common between the two pairs of participants.

Figure 6G:
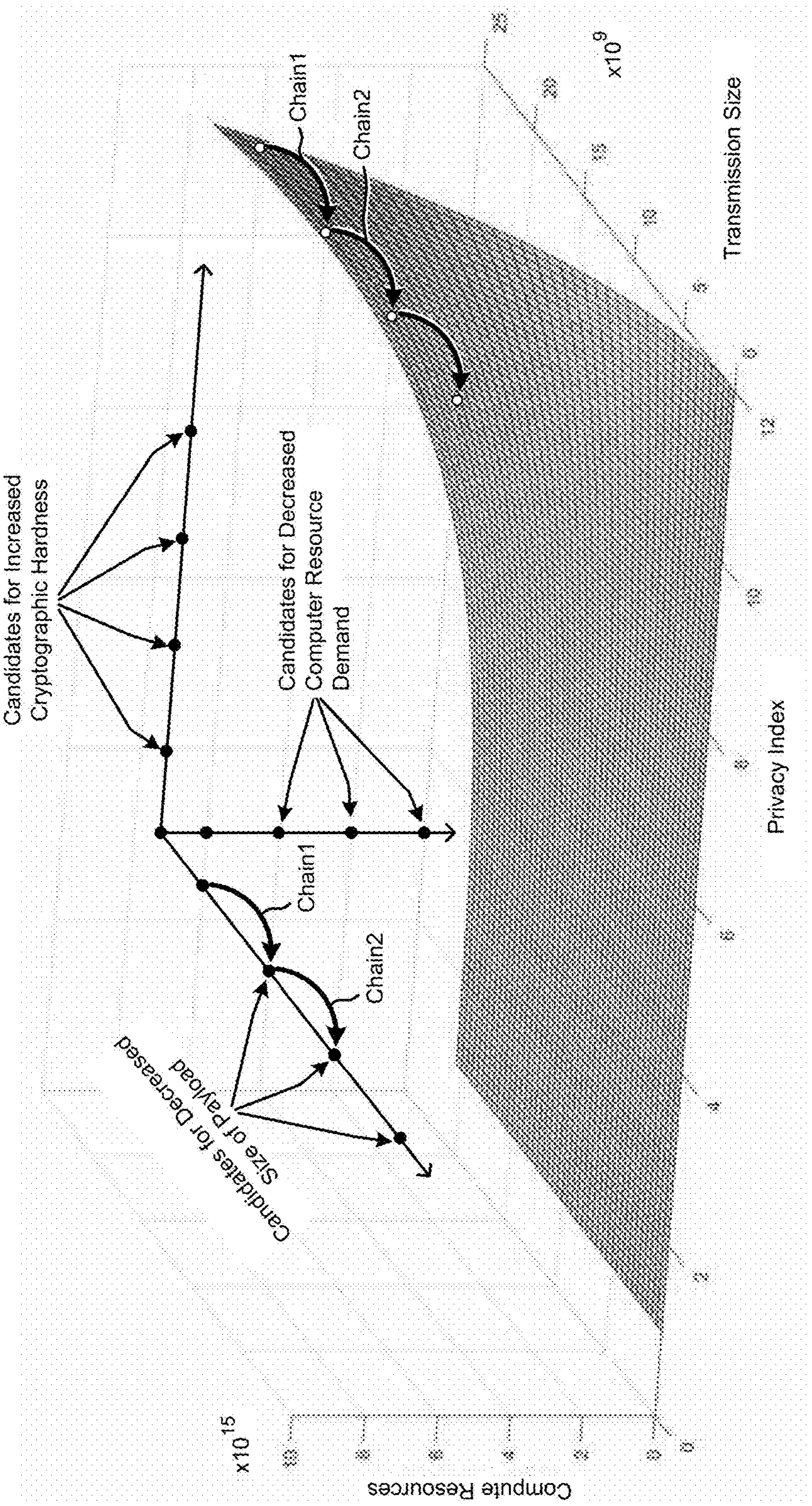
FIG. 6G shows how a surface defined by three variables can be used to optimize for a given variable in the presence of constraints on the other variables, according to a particular embodiment.

FIG. 6G shows how a surface defined by three variables 6G00 can be used to optimize for a given variable in the presence of constraints on the other variables. The surface is defined by three variables, specifically, a first variable being a privacy index on a scale from 0 to 12, a second variable being a measure of compute resources on a scale of 0 to 1015 operations needed, and a third variable on a scale of 0 to 109 being an indication of transmission size needed to share data over an Internet channel. As discussed heretofore, two parties involved in privacy-preserving analytics might need to negotiate to reach agreement on a lesser amount of computing resources demanded for a particular privacy-preserving calculation and, as such, one of the two parties might offer a particular candidate for decreased computer resource demand. Additionally or alternatively, the two parties involved in privacy-preserving analytics might need to negotiate to reach agreement on a decreased size of payload demanded for a particular privacy-preserving calculation and, as such, one of the two parties might offer a particular candidate for a decreased size of payload.

One technique to reach agreement on a decreased size of payload demanded for a particular privacy-preserving calculation involves using the surface to identify a different privacy index (e.g., possibly corresponding to a lower cryptographic hardness) such that the computer resource demanded and/or the size of payload demanded for a particular privacy-preserving calculation can be decreased (i.e., possibly in a tradeoff for a lower privacy index).

In some cases, particular chains as may be available in the agreed-upon dictionary are pre-defined so as to provide possible data reduction paths that serve to reduce the amount of computing resources needed and/or to reduce the transmission size of the payload of the shared data. In some cases, traversal across the surface might involve traversal through discrete zones of the surface. As an example, one way to reduce compute resources required and/or to reduce transmission size is to adopt an alternative cryptosystem. Some practical applications of privacy-preserving analytics are amenable to a point-in-time determination that a less private cryptosystem can be used for a particular privacy-preserving calculation, whereas other practical applications are not so amenable. For example, some privacy-preserving analytics involve data for which an extremely high degree of privacy is demanded and, as such, carrying out those privacy-preserving analytics might be more likely to involve fully homomorphic encryption of the data, even if the corresponding computing resource demand is predicted to be high and/or even if the corresponding transmission bandwidth is predicted to be high. Some such practical applications involving point-in-time fully homomorphic encryption optimization are shown and discussed as pertains to FIG. 7A and FIG. 7B.

Figure 7A:
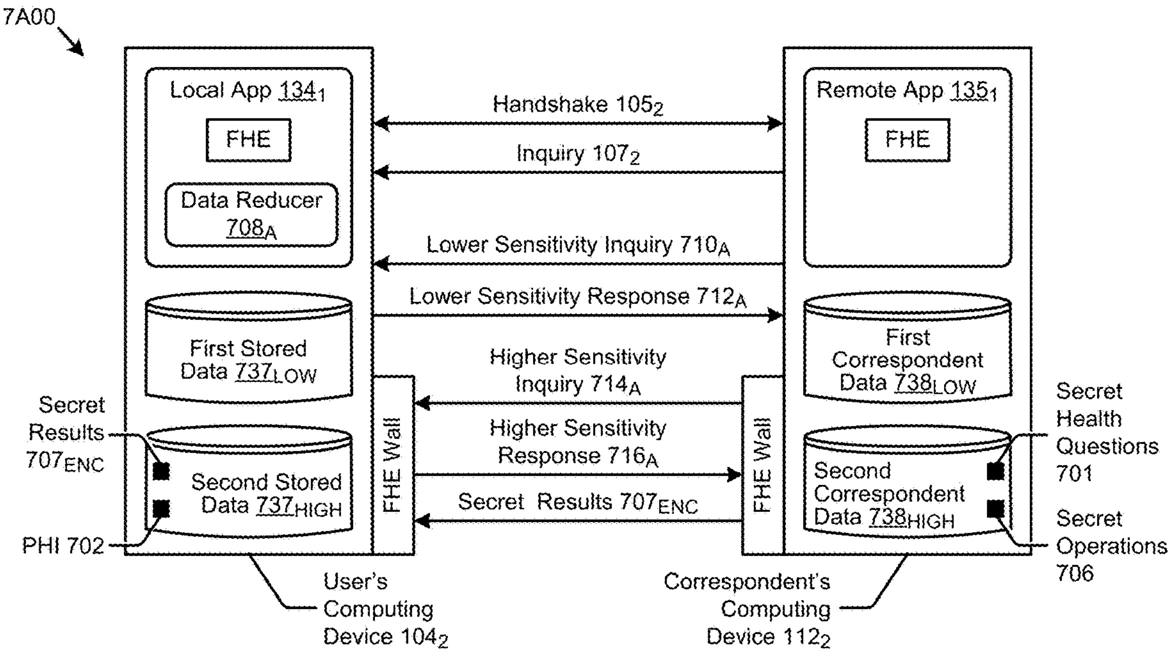
FIG. 7A illustrates a practical application of techniques for fully homomorphic encryption optimization between computers in a healthcare ecosystem, according to some embodiments.

FIG. 7A illustrates a practical application of techniques for fully homomorphic encryption optimization between computers in a healthcare ecosystem 7A00. As an option, one or more variations of healthcare ecosystem 7A00 or any aspect thereof may be implemented in the context of the architecture and functionality of the embodiments described herein. The healthcare ecosystem 7A00 or any aspect thereof may be implemented in any environment.

FIG. 7A illustrates how a local app $\mathbf{134}_1$ can use a context-specific data reducer (e.g., data reducer 708A) to split gathered data into first stored data $\mathbf{737}_{LOW}$ and second stored data $\mathbf{737}_{HIGH}$. The first stored data can be composed exclusively of data that is deemed to be of lower sensitivity, while the second stored data $\mathbf{737}_{HIGH}$ is composed of data that is deemed to be of higher sensitivity. Strictly as examples, data that is deemed to be of higher sensitivity might include protected health information (PHI). The context-specific data reducer may use any of the herein-disclosed techniques to reduce the size of data that is deemed to be sensitive.

As shown, Internet-based messaging takes place between the user's computing device $\mathbf{104}_2$ and the correspondent's computing device $\mathbf{112}_2$. The messaging may include an initialization exchange (e.g., handshake $\mathbf{105}_2$), which initialization exchange may serve to negotiate and/or establish rules for how the contents of any particular Internet protocol packet is to be formed and interpreted by the sender and receiver. For example, the initialization exchange may serve to establish that any clear text (e.g., clear text payload 332 of FIG. 3A and FIG. 3B) is to be included in a fixed length field rather than in a variable length field.

The initialization exchange might be further used to determine what cipher suites are available to be used to encrypt communications. In some cases, the initialization exchange serves to resolve which cipher suites are common between the user's computing device and the correspondent's computing device. Further, in some cases, different cipher suites are used at different times and/or under different conditions. For example, a relatively more secure (e.g., 1024-bit, 2048-bit etc.) cipher might be used during times when the quality (e.g., bandwidth) of the end-to-end Internet communication channel is high, whereas a relatively less secure (e.g., 256-bit, 512-bit etc.) cipher might be used during times when the quality (e.g., bandwidth) of the end-to-end Internet communication channel is low. Even when a relatively less secure cipher is used, the parties may agree that no exchanges are to take place that would violate any then-in-force privacy index threshold value. As used herein, a privacy index threshold value is a representation of a level of privacy (e.g., numeric value) that is considered in calculations as a constraint, below which constraint the privacy level is not to be breached.

In some situations, the then-in-force privacy index threshold value is dependent on a user setting; in other situations, the then-in-force privacy index threshold value is dependent on the kind and/or sensitivity of the subject data; in even other situations, the then-in-force privacy index threshold may fluctuate (e.g., to correspond to an increased cryptographic hardness or to correspond to a decreased cryptographic hardness) based on the then-current availability of computing resources and/or the then-current conditions of the end-to-end Internet communication channel.

As shown, the Internet exchange proceeds when the correspondent's computing device sends a call (e.g., inquiry $\mathbf{107}_2$) to the user's computing device. The call establishes parameters that are used in further exchanges. Strictly as examples, an inquiry pertaining to the then-current availability of computing resources at the user's computing device might be deemed to be a lower sensitivity inquiry 710A, whereas an inquiry pertaining to any aspect of the user's protected health information (e.g., PHI 702) might be deemed to be a higher sensitivity inquiry 714A.

Responses by the user's computing device might be carried out with respect to the sensitivity of the inquiry. For example, in response to a lower sensitivity inquiry, the user's computing device might send one or more lower sensitivity responses (e.g., any number of occurrences of a lower sensitivity response $712_A$) whereas, in response to a higher sensitivity inquiry, the user's computing device might send one or more higher sensitivity responses (e.g., any number of occurrences of a higher sensitivity response $716_A$). In this embodiment, and as shown, higher sensitivity inquiries and higher sensitivity responses are carried out using fully homomorphic encryption (e.g., through an FHE Wall, as shown), whereas lower sensitivity inquiries and lower sensitivity responses are carried out using privacy-protecting techniques that do not involve fully homomorphic encryption.

Fully homomorphic encryption facilitates performance of secret operations 706 over protected health information that is encrypted and shared with the correspondent's computing device. The specific protected health information that is encrypted and shared with the correspondent's computing device may be selected in response to one or more secret health questions 701 that are selected and shared with the user's computing device. When at least some of the secret operations 706 have been performed over protected health information (e.g., PHI 702), secret results $707_{ENC}$ are delivered to the user's computing device to be stored in second stored data $737_{HIGH}$.

In some embodiments, secret health questions 701, and/or secret operations 706, and/or PHI 702, and/or secret results $707_{ENC}$ are stored in encrypted form in a highly secure area (e.g., within second correspondent data $738_{HIGH}$). The highly secure area might include only data in encrypted form (e.g., as encrypted objects), whereas data of a sufficiently lower sensitivity might be stored in unencrypted form (e.g., within first correspondent data $738_{LOW}$) for easy access (e.g., in a database).

As can now be seen, the healthcare ecosystem 7A00 supports methods for performing negotiated resource-efficient privacy-preserving transactions involving protected health data. Specifically, handshake $105_2$ serves to establish an Internet communication channel between the user device and the correspondent device. Subsequently, in response to a health data inquiry (e.g., a secret health question) the local app at the user's computing device performs: (1) preprocessing to form a set of protected health data comprising reduced-size protected health data, followed by (2) encrypting, using a fully homomorphic encryption algorithm, the reduced-size protected health data.

The encrypted reduced-size protected health data may be used to form an individual segment of a multi-segment response. Additional individual segments of the multi-segment response may comprise additional user data that is encrypted using an encryption algorithm other than the fully homomorphic encryption algorithm. The foregoing segments are transmitted to the correspondent device where privacy-preserving analytics (e.g., secret operations 706) are performed over the encrypted reduced-size protected health data.

As used herein a fully homomorphic encryption algorithm is a cryptosystem that supports arbitrary computation on ciphertexts. Application of fully homomorphic encryption enables the construction of ciphertext programs (i.e., sequences of arbitrary computations on ciphertexts) that achieve any functionality. Such ciphertext programs can be run on encrypted inputs to produce encrypted results such that a decrypted version of the encrypted results will match the ciphertext program results had the ciphertext program been run on unencrypted inputs. Since such a ciphertext program need never decrypt its inputs to return an encrypted result, a user's computer can ask a correspondent's computer of an untrusted party to execute a ciphertext program and return encrypted results without the computer of the untrusted party ever having a cipher key to decrypt the inputs to the ciphertext program.

Figure 7B:
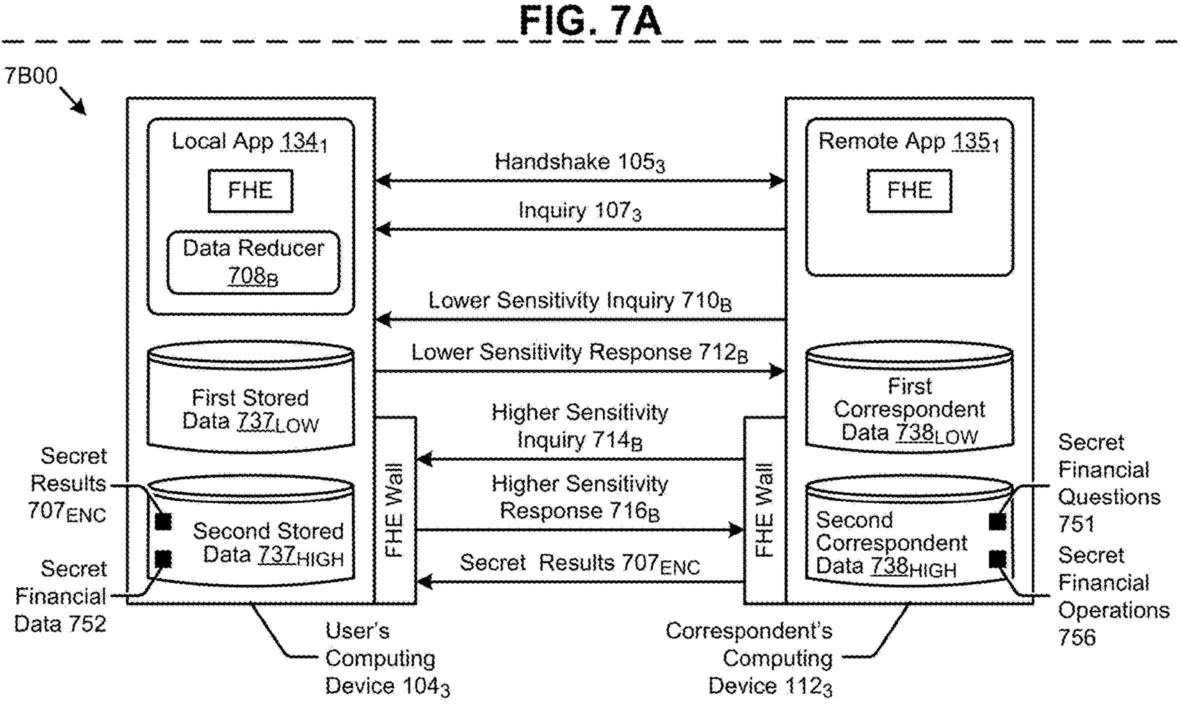
FIG. 7B illustrates a practical application of techniques for fully homomorphic encryption optimization between computers in a financial services ecosystem, according to some embodiments.

FIG. 7B illustrates a practical application of techniques for fully homomorphic encryption optimization between computers in a financial services ecosystem 7B00. As an option, one or more variations of financial services ecosystem 7B00 or any aspect thereof may be implemented in the context of the architecture and functionality of the embodiments described herein. The financial services ecosystem 7B00 or any aspect thereof may be implemented in any environment.

FIG. 7B illustrates how a local app $134_1$ can use a context-specific data reducer (e.g., data reducer 708B) to split gathered data into first stored data $737_{LOW}$ and second stored data $737_{HIGH}$. The first stored data $737_{LOW}$ can be composed exclusively of data that is deemed to be of lower sensitivity, while the second stored data $737_{HIGH}$ is composed of data that is deemed to be of higher sensitivity. Strictly as examples, data that is deemed to be of higher sensitivity might include a user's financial information. The context-specific data reducer may use any of the herein-disclosed techniques to reduce the size of data that is deemed to be sensitive.

As shown, Internet-based messaging takes place between the user's computing device $104_3$ and the correspondent's computing device $112_3$. The messaging may include an initialization exchange (e.g., handshake $105_3$), which initialization exchange may serve to negotiate and/or establish rules for how the contents of any particular Internet protocol packet is to be formed and interpreted by the sender and receiver.

As shown, the Internet exchange proceeds when the correspondent's computing device sends a call (e.g., inquiry $107_3$) to the user's computing device. The call establishes parameters that are used in further exchanges. Strictly as examples, an inquiry pertaining to the then-current availability of computing resources at the user's computing device might be deemed to be a lower sensitivity inquiry $710_B$, whereas an inquiry pertaining to any aspect of the user's financial information (e.g., secret financial data 752) might be deemed to be a higher sensitivity inquiry 714B.

Responses by the user's computing device might be carried out with respect to the sensitivity of the inquiry. For example, in response to a lower sensitivity inquiry, the user's computing device might send one or more lower sensitivity responses (e.g., any number of occurrences of a lower sensitivity response $712_B$) whereas, in response to a higher sensitivity inquiry, the user's computing device might send one or more higher sensitivity responses (e.g., any number of occurrences of a higher sensitivity response $716_B$). In this embodiment, and as shown, higher sensitivity inquiries and higher sensitivity responses are carried out using fully homomorphic encryption (e.g., through an FHE Wall, as shown), whereas lower sensitivity inquiries and lower sensitivity responses are carried out using privacy-protecting techniques that do not involve fully homomorphic encryption.

Fully homomorphic encryption facilitates performance of secret financial operations 756 over financial information that is encrypted and shared with the correspondent's computing device. The specific protected health information that is encrypted and shared with the correspondent's computing device may be selected in response to one or more secret financial questions 751 that are selected and shared with the user's computing device. When at least some of the secret financial operations 756 have been performed over the financial information (e.g., secret financial data 752), secret results $\mathbf{707}_{ENC}$ are delivered to the user's computing device to be stored in second stored data $\mathbf{737}_{HIGH}$.

In some embodiments, secret financial questions 751, and/or secret financial operations 756, and/or secret financial data 752, and/or secret results $\mathbf{707}_{ENC}$ are stored in encrypted form in a highly secure area (e.g., within second correspondent data $\mathbf{738}_{HIGH}$). The highly secure area might include only data in encrypted form (e.g., as encrypted objects), whereas data of a sufficiently lower sensitivity might be stored in unencrypted form (e.g., within first correspondent data $\mathbf{738}_{LOW}$) for easy access (e.g., in a database).

For example, in a financial setting, a variable denoting "generally interested in loan products" could be treated as low sensitivity, whereas a list of the top three internet search phrases recently employed by the applicant (e.g., "Shall I declare bankruptcy?", or "What shall I do if I am audited by the IRS?", or "Is loan fraud a federal felony?") could be denoted as higher sensitivity data. Sensitivity of data may be correlated to a range such as "High", "Medium", or "Low". Moreover data within one range might be tagged with a designation of a range within the range. For example, the personal identity of the top three people regularly contacted by the applicant via text messaging could be treated as the most sensitive data within the "High" range.

As can now be seen, the financial services ecosystem 7B00 supports methods for performing negotiated resource-efficient privacy-preserving transactions involving protected financial data. Specifically, handshake $\mathbf{105}_2$ serves to establish an Internet communication channel between the user device and the correspondent device. Subsequently, in response to a financial data inquiry (e.g., a secret financial question), the local app at the user's computing device performs: (1) preprocessing to form a set of protected financial data comprising reduced-size protected financial data, followed by (2) encrypting, using a fully homomorphic encryption algorithm, the reduced-size protected financial data.

The encrypted reduced-size protected financial data may be used to form an individual segment of a multi-segment response. Additional individual segments of the multi-segment response may comprise additional user data that is encrypted using an encryption algorithm other than the fully homomorphic encryption algorithm. The foregoing segments are transmitted to the correspondent device where privacy-preserving analytics (e.g., secret financial operations 756) are performed over the encrypted reduced-size protected financial data.

Additional Embodiments of the Disclosure

Additional Practical Application Examples

Figure 8A:
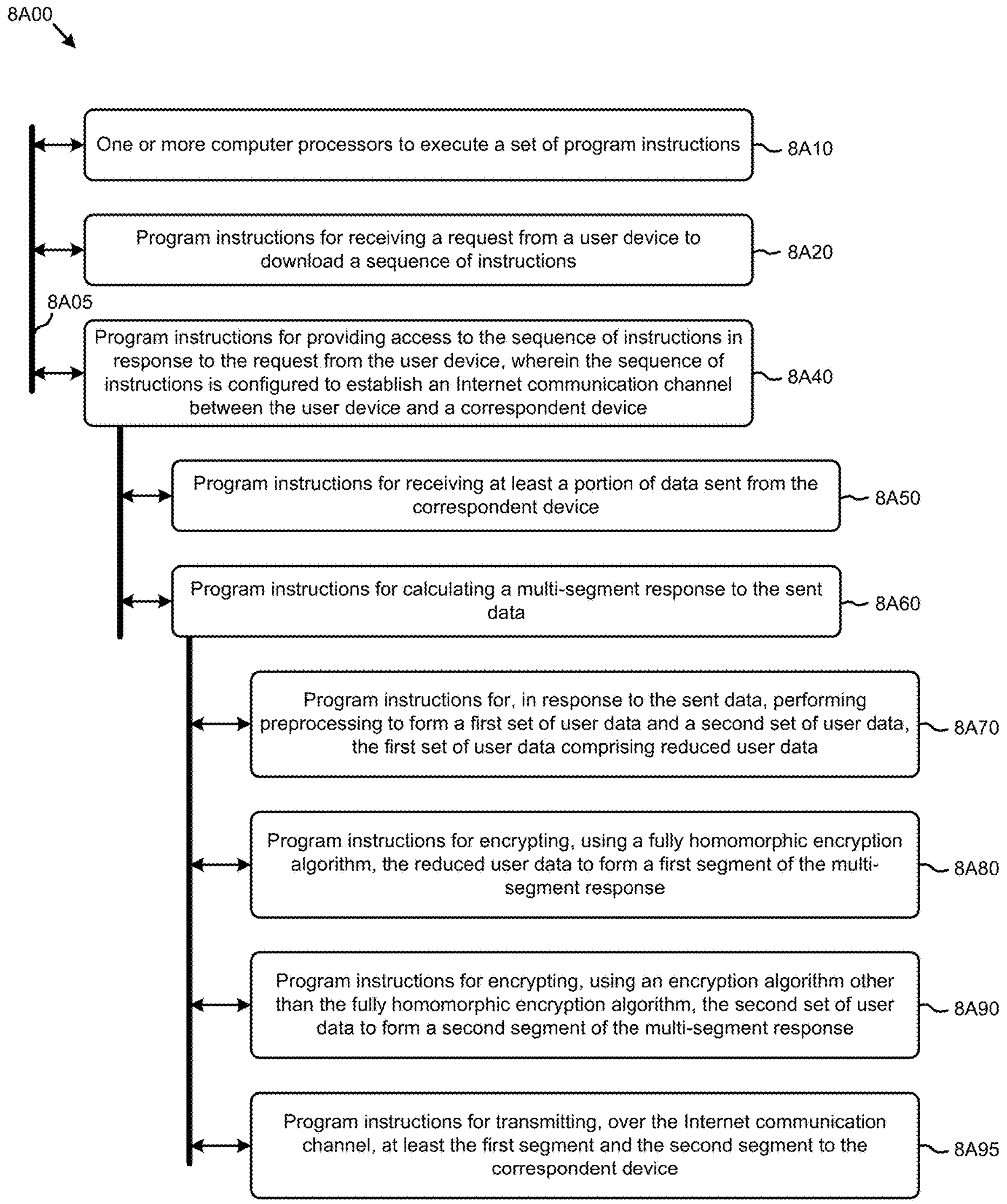
FIG. 8A and FIG. 8B depict system components as arrangements of computing modules that are interconnected so as to implement certain of the herein-disclosed embodiments.

FIG. 8A depicts a system 8A00 as an arrangement of computing modules that are interconnected so as to operate cooperatively to implement certain of the herein-disclosed embodiments. This and other embodiments present particular arrangements of elements that, individually or as combined, serve to form improved technological processes that address how to achieve high-performance multi-party privacy-preserving analytics even when some analytics require homomorphic encryption. The partitioning of system 8A00 is merely illustrative and other partitions are possible.

Variations of the foregoing may include more or fewer of the shown modules. Certain variations may perform more or fewer (or different) steps and/or certain variations may use data elements in more, or in fewer, or in different operations. As an option, the system 8A00 may be implemented in the context of the architecture and functionality of the embodiments described herein. Of course, however, the system 8A00 or any operation therein may be carried out in any desired environment.

The system 8A00 comprises at least one processor and at least one memory, the memory serving to store program instructions corresponding to the operations of the system. As shown, an operation can be implemented in whole or in part using program instructions accessible by a module. The modules are connected to a communication path 8A05, and any operation can communicate with any other operations over communication path 8A05. The modules of the system can, individually or in combination, perform method operations within system 8A00. Any operations performed within system 8A00 may be performed in any order unless as may be specified in the claims.

The shown embodiment implements a portion of a computer system, presented as system 8A00, comprising one or more computer processors to execute a set of program code instructions (module 8A10) and modules for accessing memory to hold program code instructions to perform: receiving a request from a user device to download a sequence of instructions (module 8A20); providing access to the sequence of instructions in response to the request from the user device, wherein the sequence of instructions is configured to establish an Internet communication channel between the user device and a correspondent device (module 8A40).

The sequence of instructions may include program instructions for receiving at least a portion of the sent data from the correspondent device (module 8A50); program instructions for calculating a multi-segment response to the sent data by (module 8A60). The calculation aspects of the multi-segment response might be based in part on the then-current conditions of the Internet channels and/or based in part on the then-current availability of computing resources. The sequence of instructions are further configured as program instructions for, in response to the sent data, performing preprocessing to form a first set of user data and a second set of user data, the first set of user data comprising reduced user data (module 8A70); program instructions for encrypting, using a fully homomorphic encryption algorithm, the reduced user data to form a first segment of the multi-segment response (module 8A80). The reduced user data may be reduced with respect to accuracy and/or in size, or both. For example, a fixed point value of "1.0" as represented by the string, "1.0000000" (i.e., 10 bytes) might be bit-wise larger than a four byte computer word (i.e., 24-bit mantissa and 8 bit exponent) that is a floating point representation of the value "1.0".

The sequence of instructions may further include program instructions for encrypting, using an encryption algorithm other than the fully homomorphic encryption algorithm, the second set of user data to form a second segment of the multi-segment response (module 8A90); and program instructions for transmitting, over the Internet communication channel, at least the first segment and the second segment to the correspondent device (module 8A95).

Still further, some embodiments include variations in the operations performed, and some embodiments include variations of aspects of the data elements used in the operations.

Figure 8B:
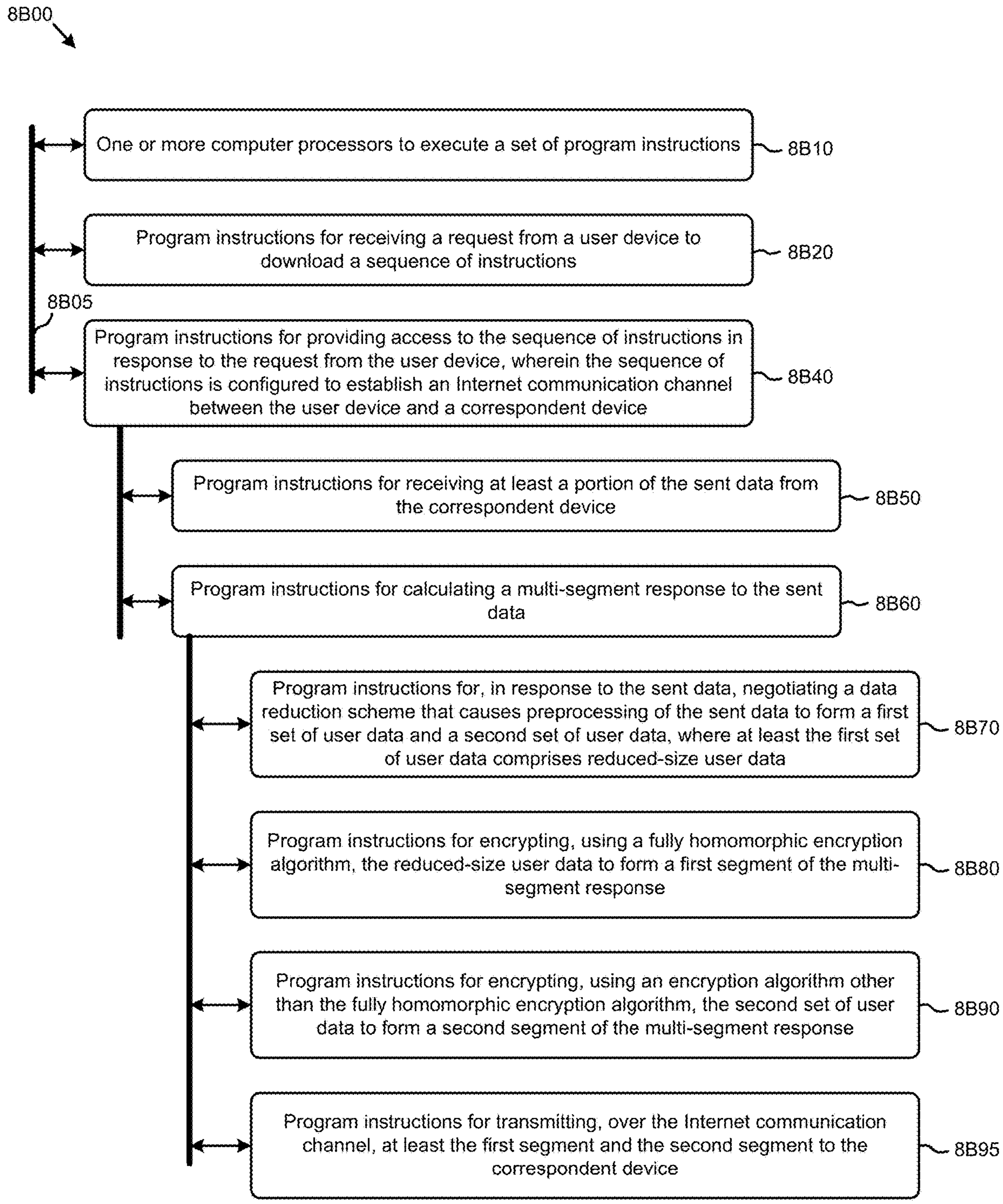

FIG. 8B depicts a system 8B00 as an arrangement of computing modules that are interconnected so as to operate cooperatively to implement certain of the herein-disclosed embodiments. This and other embodiments present particular arrangements of elements that, individually or as combined, serve to form improved technological processes that address how to achieve high-performance multi-party privacy-preserving analytics even when some analytics require homomorphic encryption. The partitioning of system 8B00 is merely illustrative and other partitions are possible.

Variations of the foregoing may include more or fewer of the shown modules. Certain variations may perform more or fewer or different steps and/or certain variations may use data elements in more, or in fewer, or in different operations. As an option, the system 8B00 may be implemented in the context of the architecture and functionality of the embodiments described herein. Of course, however, the system 8B00 or any operation therein may be carried out in any desired environment.

The system 8B00 comprises at least one processor and at least one memory, the memory serving to store program instructions corresponding to the operations of the system. As shown, an operation can be implemented in whole or in part using program instructions accessible by a module. The modules are connected to a communication path 8B05, and any operation can communicate with any other operations over communication path 8B05. The modules of the system can, individually or in combination, perform method operations within system 8B00. Any operations performed within system 8B00 may be performed in any order unless as may be specified in the claims.

The shown embodiment implements a portion of a computer system, presented as system 8B00, comprising one or more computer processors to execute a set of program code instructions (module 8B10) and modules for accessing memory to hold program code instructions to perform: receiving a request from a user device to download a sequence of instructions (module 8B20); providing access to the sequence of instructions in response to the request from the user device, wherein the sequence of instructions is configured to establish an Internet communication channel between the user device and a correspondent device (module 8B40).

The sequence of instructions may include program instructions for receiving at least a portion of the sent data from the correspondent device (module 8B50); and program instructions for calculating a multi-segment response to the sent data by (module 8B60). Various aspects of the multi-segment response might be determined based in part on the then-current conditions of the Internet channels and/or based in part on the then-current availability of computing resources.

The sequence of instructions are further configured as program instructions for, in response to the sent data, negotiating a data reduction scheme that causes preprocessing of the sent data to form a first set of user data and a second set of user data, where at least the first set of user data comprises reduced-size user data (module 8B70). The sequence of instructions further comprises program instructions for encrypting, using a fully homomorphic encryption algorithm, the reduced-size user data to form a first segment of the multi-segment response (module 8B80); program instructions for encrypting, using an encryption algorithm other than the fully homomorphic encryption algorithm, the second set of user data to form a second segment of the multi-segment response (module 8B90); and program instructions for transmitting, over the Internet communication channel, at least the first segment and the second segment to the correspondent device (module 8B95).

Still further, some embodiments include variations in the operations performed, and some embodiments include variations of aspects of the data elements used in the operations.

System Architecture Overview

Additional System Architecture Examples

Figure 9A:
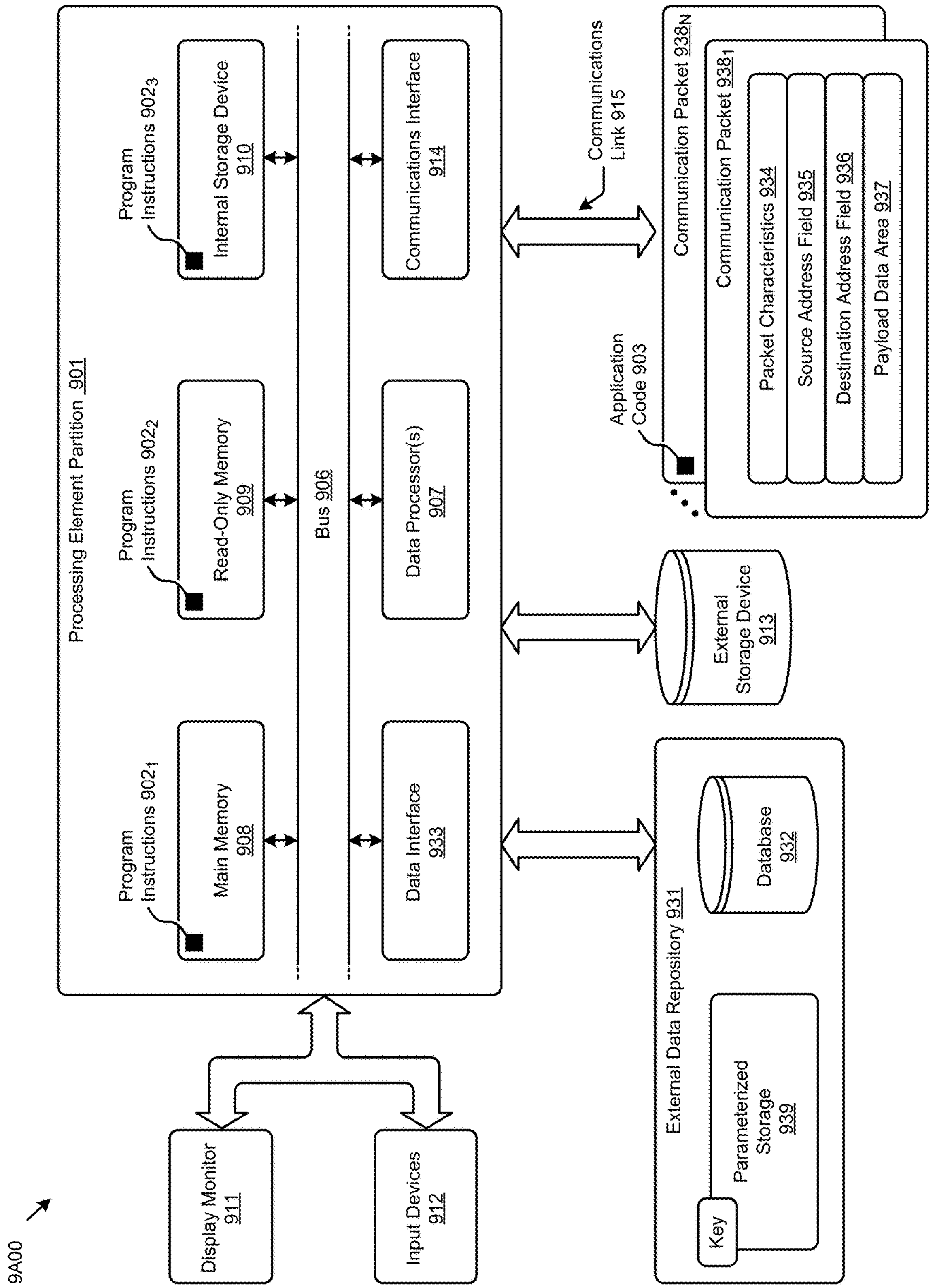
FIG. 9A and FIG. 9B present block diagrams of computer system architectures having components suitable for implementing embodiments of the present disclosure, and/or for use in the herein-described environments.

FIG. 9A depicts a block diagram of an instance of a computer system 9A00 suitable for implementing embodiments of the present disclosure. Computer system 9A00 includes a bus 906 or other communication mechanism for communicating information. The bus interconnects subsystems and devices such as a central processing unit (CPU), or a multi-core CPU (e.g., data processor 907), a system memory (e.g., main memory 908, or an area of random access memory (RAM)), a non-volatile storage device or non-volatile storage area (e.g., read-only memory 909), an internal storage device 910 or external storage device 913 (e.g., magnetic or optical), a data interface 933, a communications interface 914 (e.g., PHY, MAC, Ethernet interface, modem, etc.). The aforementioned components are shown within processing element partition 901, however other partitions are possible. Computer system 9A00 further comprises a display 911 (e.g., CRT or LCD), various input devices 912 (e.g., keyboard, cursor control), and an external data repository 931.

According to an embodiment of the disclosure, computer system 9A00 performs specific operations by data processor 907 executing one or more sequences of one or more program instructions contained in a memory. Such instructions (e.g., program instructions $\mathbf{902}_1$, program instructions $\mathbf{902}_2$, program instructions $\mathbf{902}_3$, etc.) can be contained in or can be read into a storage location or memory from any computer readable/usable storage medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination thereof.

According to an embodiment of the disclosure, computer system 9A00 performs specific networking operations using one or more instances of communications interface 914. Instances of communications interface 914 may comprise one or more networking ports that are configurable (e.g., pertaining to speed, protocol, physical layer characteristics, media access characteristics, etc.) and any particular instance of communications interface 914 or port thereto can be configured differently from any other particular instance. Portions of a communication protocol can be carried out in whole or in part by any instance of communications interface 914, and data (e.g., packets, data structures, bit fields, etc.) can be positioned in storage locations within communications interface 914, or within system memory, and such data can be accessed (e.g., using random access addressing, or using direct memory access DMA, etc.) by devices such as data processor 907.

Communications link 915 can be configured to transmit (e.g., send, receive, signal, etc.) any types of communications packets (e.g., communication packet $\mathbf{938}_1$, communication packet $\mathbf{938}_N$) comprising any organization of data items. The data items can comprise a payload data area 937, a destination address 936 (e.g., a destination IP address), a source address 935 (e.g., a source IP address), and can include various encodings or formatting of bit fields to populate packet characteristics 934. In some cases, the packet characteristics include a version identifier, a packet or payload length, a traffic class, a flow label, etc. In some cases, payload data area 937 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to data processor 907 for execution. Such a medium may take many forms including, but not limited to, non-volatile media and volatile media. Non-volatile media includes, for example, optical or magnetic disks such as disk drives or tape drives. Volatile media includes dynamic memory such as RAM.

Common forms of computer readable media include, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of external data repository 931, which in turn can be formatted into any one or more storage areas, and which can comprise parameterized storage 939 accessible by a key (e.g., filename, table name, block address, offset address, etc.).

Execution of the sequences of instructions to practice certain embodiments of the disclosure are performed by a single instance of a computer system 9A00. According to certain embodiments of the disclosure, two or more instances of computer system 9A00 coupled by a communications link 915 (e.g., LAN, public switched telephone network, or wireless network) may perform the sequence of instructions required to practice embodiments of the disclosure using two or more instances of components of computer system 9A00.

Computer system 9A00 may transmit and receive messages such as data and/or instructions organized into a data structure (e.g., communications packets). The data structure can include program instructions (e.g., application code 903), communicated through communications link 915 and communications interface 914. Received program instructions may be executed by data processor 907 as it is received and/or stored in the shown storage device or in or upon any other non-volatile storage for later execution. Computer system 9A00 may communicate through a data interface 933 to a database 932 on an external data repository 931. Data items in a database can be accessed using a primary key (e.g., a relational database primary key).

Processing element partition 901 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a data processor 907. Some embodiments include one or more special-purpose hardware components (e.g., power control, logic, sensors, transducers, etc.). Some embodiments of a module include instructions that are stored in a memory for execution so as to facilitate operational and/or performance characteristics pertaining to performing negotiated resource-efficient privacy-preserving transactions involving large amounts of mixed kinds of data. A module may include one or more state machines and/or combinational logic used to implement or facilitate the operational and/or performance characteristics pertaining to performing negotiated resource-efficient privacy-preserving transactions involving large amounts of mixed kinds of data.

Various implementations of database 932 comprise storage media organized to hold a series of records or files such that individual records or files are accessed using a name or key (e.g., a primary key or a combination of keys and/or query clauses). Such files or records can be organized into one or more data structures (e.g., data structures used to implement or facilitate aspects of performing negotiated resource-efficient privacy-preserving transactions involving large amounts of mixed kinds of data). Such files, records, or data structures can be brought into and/or stored in volatile or non-volatile memory. More specifically, the occurrence and organization of the foregoing files, records, and data structures improve the way that the computer stores and retrieves data in memory, for example, to improve the way data is accessed when the computer is performing operations pertaining to performing negotiated resource-efficient privacy-preserving transactions involving large amounts of mixed kinds of data, and/or for improving the way data is manipulated when performing computerized operations pertaining to preprocessing sensitive data items to match payload content volume with communication channel or processing capabilities.

Figure 9B:
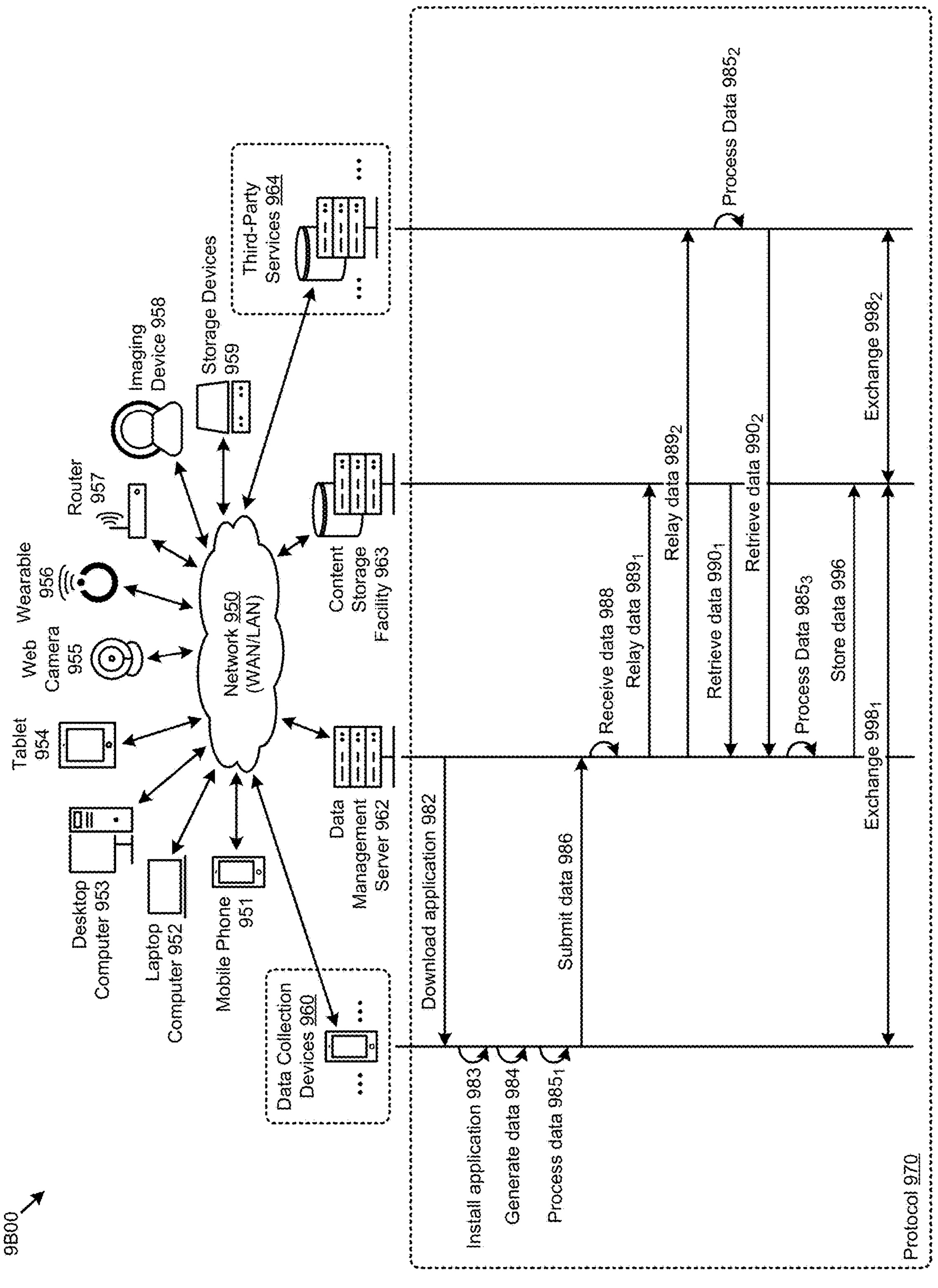

FIG. 9B depicts an environment 9B00 in which embodiments of the present disclosure can operate. As an option, one or more aspects shown in environment 9B00 or any combination of components of the environment may be implemented in the context of the architecture and functionality of the embodiments described herein.

As shown, environment 9B00 comprises various computing systems (e.g., servers and devices) interconnected by a network 950. The network 950 can comprise any combination of a wide area network (e.g., WAN), local area network (e.g., LAN), cellular network, wireless LAN (e.g., WLAN), or any such means for enabling communication of computing systems. Some or all or network 950 can also be referred to as "the Internet" or as an "Internet". The example environment 9B00 comprises data collection devices 960, an instance of a data management server 962, an instance of a content storage facility 963, and optional instances of third-party services 964, all of which may communicate with any other operational elements over network 950.

The servers and devices shown in environment 9B00 can represent any single computing system with dedicated hardware and software, or the servers and devices shown in environment 9B00 can represent multiple computing systems connected together (e.g., in a server farm, or in a host farm, etc.). In some cases, multiple computing systems share resources. For example, data management server 962 and content storage facility 963 might be closely coupled (e.g., co-located) and/or might be implemented using the same hardware platform.

The environment 9B00 may further comprise a variety of other devices such as a mobile phone 951, a laptop 952, a desktop computer 953, a tablet 954, a web camera 955, a wearable device 956, etc. The environment may still further comprise computing equipment such as a router 957, an imaging device 958 (e.g., CT scanner, MRI machine, etc.), and any number of storage devices 959, etc. Some or all of the foregoing computing devices and computing equipment may support software (e.g., a browser, mobile application, etc.) and hardware (e.g., an LCD display, a graphics processing unit, display, monitor, etc.) capable of processing and displaying information (e.g., an image, a web page, etc.). Any of the foregoing computing devices or computing equipment can serve as or augment the capabilities of one of the data collection devices 960.

In some embodiments, any particular one of the data collection devices 960 can be used in conjunction with a different particular one of the data collection devices to determine the location and/or identity of a user.

As shown, the computing devices and computing equipment can perform a set of high-level interactions (e.g., operations, messages, etc.) in a protocol 970. Specifically, the protocol can represent interactions that may occur in systems that facilitate performing negotiated resource-efficient privacy-preserving transactions involving large amounts of mixed kinds of data.

An application or app can be generated using any known techniques. Such an application or app cooperates with other operational elements of the environment to perform operations that facilitate to performing negotiated resource-efficient privacy-preserving transactions involving large amounts of mixed kinds of data, and/or to perform computerized operations pertaining to preprocessing sensitive data items to match payload content volume with communication channel or processing capabilities. The application or app may be configured so as to operate on any one or more data collection devices. As shown, any of the data collection devices 960 can download such an application or app (operation 982) from data management server 962 or another other server, check the download for integrity, and then install the application or app (operation 983). The application can be used to capture and/or generate data (operation 984), process the captured or generated data (operation $\mathbf{985}_1$), and submit data (message 986) to the data management server.

To perform one or more operations of protocol 970, data management server 962 is configured to receive data (operation 988) corresponding to the data submitted from the data collection devices. Such received data may be relayed or otherwise transmitted (message 9891 or message $\mathbf{989}_2$) to downstream computing equipment such as the shown one or more third-party services 964. The third-party services can process such data (e.g., operation $\mathbf{985}_2$), possibly in response to the specific contents of the relayed or otherwise transmitted messages.

Furthermore, data management server 962 may retrieve data (message $\mathbf{990}_1$) from any storage facility, including from content storage facility 963 or from any one or more of the third-party services (message $\mathbf{990}_2$).

An instance of data management server 962 can be configured to autonomously (e.g., under program control) analyze or otherwise process any received data (operation $\mathbf{985}_3$)). Moreover, example instances of a data management server 962 can be configured to store data at any storage facility including at a content storage facility 963, (message 996) or at any one or more storage devices of the third-party services 964.

In some cases, the third-party services produce additional data that is derived, directly or indirectly, from the data received from the data collection devices. In some cases, and as shown, such additional data might be retrieved (message $\mathbf{990}_2$) and analyzed or otherwise processed by data management server 962 (operation $\mathbf{985}_3$). As such, data can be transformed in a cascading fashion. Specifically, data can be initially processed at one or more of the data collection devices, then alternatively or additionally, the resulting data can be processed at the data management server, then alternatively or additionally, the still further resulting data can be processed at the third-party services. Furthermore, in some cases, data can be exchanged between content storage facility 963, and any of the data collection devices 960 (exchange $\mathbf{998}_1$). Additionally, or alternatively, data can be exchanged between content storage facility 963 and any of the third-party services 964 (exchange $\mathbf{998}_2$).

In the foregoing specification, the disclosure has been described with reference to specific embodiments thereof. It will, however, be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are to be regarded in an illustrative sense rather than in a restrictive sense.

What is claimed is:

1. A method for performing resource-efficient privacy-preserving transactions over one or more kinds of data, the method comprising:

establishing an Internet communication channel between a user device and a correspondent device;

receiving a data inquiry from the correspondent device;

preparing a response to the data inquiry by:

in response to the data inquiry, negotiating a data reduction scheme that causes preprocessing to modify the one or more kinds of data to form one or more reduced-size instances of the one or more kinds of data;

encrypting at least a portion of the reduced-size instances of the one or more kinds of data to form a first segment of the response; and transmitting, over the Internet communication channel, at least a portion of the first segment of the response to the correspondent device.

2. The method of claim 1, wherein the preprocessing comprises at least one of, determination of a kind value corresponding to the at least a portion of the one or more kinds of data, determination of a sensitivity value corresponding to the at least a portion of the one or more kinds of data, determination of a reduction scheme corresponding to the at least a portion of the one or more kinds of data, or determination of a homomorphic encryption algorithm.

3. The method of claim 2, wherein the preprocessing comprises use of at least one of, a kind classifier, or a sensitivity classifier.

4. The method of claim 2, wherein the preprocessing comprises at least one of, an operation to isolate a portion of an image, or an operation to perform edge detection on the image, or an operation to downsample the image.

5. The method of claim 2, wherein the preprocessing comprises determining bandwidth availability of one or more end-to-end Internet communication channels before determining feasibility of a data reduction operation.

6. The method of claim 1, further comprising:

in response to the data inquiry, initiating a protocol with another party and carrying out the protocol to negotiate set of optimization parameters.

7. The method of claim 6, further comprising: determining a particular feasible data reduction scheme.

8. The method of claim 1, wherein a first party corresponding to the user device enforces a greater privacy index than does a second party corresponding to the correspondent device.

9. The method of claim 1, further comprising:

consulting a data reduction transform dictionary.

10. The method of claim 9, further comprising, negotiating a particular instance of the data reduction transform dictionary.

11. The method of claim 9, wherein at least some entries of the data reduction transform dictionary comprise at least one of, an indication of an extent to which a particular operation reduces a particular type of input data, an indication of whether a particular data reduction operation corresponds to a more secure encryption scheme, or an indication of whether a particular chain corresponds to a more secure encryption scheme.

12. The method of claim 1, wherein a second party corresponding to the correspondent device enforces a greater privacy index than does a first party corresponding to the user device.

13. The method of claim 1, wherein the data reduction scheme is negotiated based at least in part on an optimization priority.

14. The method of claim 1, wherein the negotiating comprises offering at least one candidate for an increased cryptographic hardness.

15. The method of claim 1, wherein at least one correspondent in the negotiating evaluates an optimization function that determines whether to counter an offer or to accept the offer.

16. The method of claim 1, wherein the data reduction scheme is negotiated based at least in part on then-current conditions of the Internet channels and/or based at least in part on then-current availability of computing resources.

17. The method of claim 16, wherein the data reduction scheme comprises a sequence of at least one reduction technique.

18. The method of claim 1, wherein the negotiating comprises offering at least one candidate for a decreased size of payload.

19. The method of claim 1, wherein the negotiating comprises offering at least one candidate for a decreased computer resource demand.

20. The method of claim 1, wherein the negotiating comprises offering at least one candidate for an increased cryptographic hardness.

* * * * *